(12) United States Patent
Martin et al.

US010667515B2

(10) Patent No.: US 10,667,515 B2
(45) Date of Patent: Jun. 2, 2020

(54) (S)-5-ETHYNYL-ANABASINE, DERIVATIVES THEREOF, AND RELATED COMPOSITIONS AND METHODS OF MAKING AND USING

(71) Applicant: IOWA STATE UNIVERSITY RESEARCH FOUNDATION, INC., Ames, IA (US)

(72) Inventors: Richard J. Martin, Ames, IA (US); Alan P. Robertson, Ames, IA (US); Brett VanVeller, Ames, IA (US); Xiangwei Du, Ames, IA (US); Fudan Zheng, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/650,936

(22) Filed: Jul. 16, 2017

(65) Prior Publication Data
US 2018/0139961 A1    May 24, 2018

Related U.S. Application Data

(60) Provisional application No. 62/424,496, filed on Nov. 20, 2016.

(51) Int. Cl.
*A01N 43/40* (2006.01)
*C07D 401/04* (2006.01)
*A01N 55/00* (2006.01)
*A61K 31/4406* (2006.01)

(52) U.S. Cl.
CPC ............. *A01N 43/40* (2013.01); *A01N 55/00* (2013.01); *A61K 31/4406* (2013.01); *C07D 401/04* (2013.01)

(58) Field of Classification Search
None
See application file for complete search history.

(56) References Cited

U.S. PATENT DOCUMENTS

| 5,723,477 A  * | 3/1998 | McDonald | ........... C07D 401/04 514/211.15 |
| 2008/0188527 A1 * | 8/2008 | Cashman | ............. C07D 401/04 514/341 |

* cited by examiner

*Primary Examiner* — Sue X Liu
*Assistant Examiner* — Thor Nielsen
(74) *Attorney, Agent, or Firm* — Carol Larcher; Larcher & Chao Law Group

(57) ABSTRACT

(S)-5-ethynyl-anabasine and derivatives thereof; composition comprising same and a carrier; methods of treating an animal; method of protecting a plant from a pest; and methods of making compound and derivatives.

8 Claims, 10 Drawing Sheets

Specification includes a Sequence Listing.

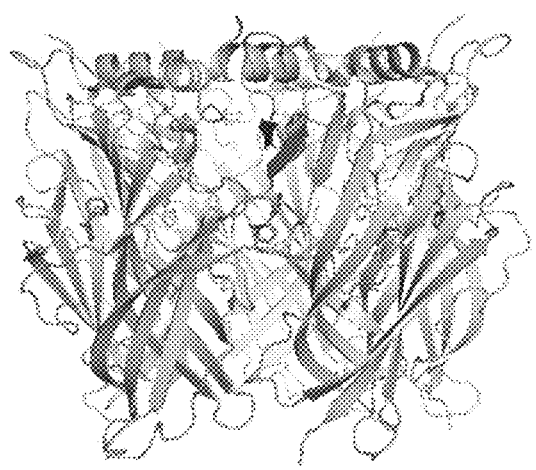
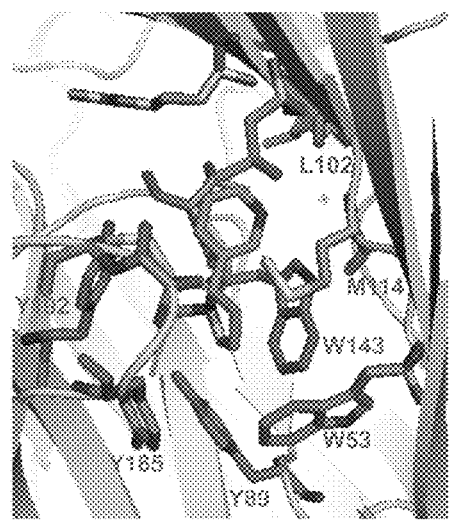
FIG. 2A  FIG. 2B
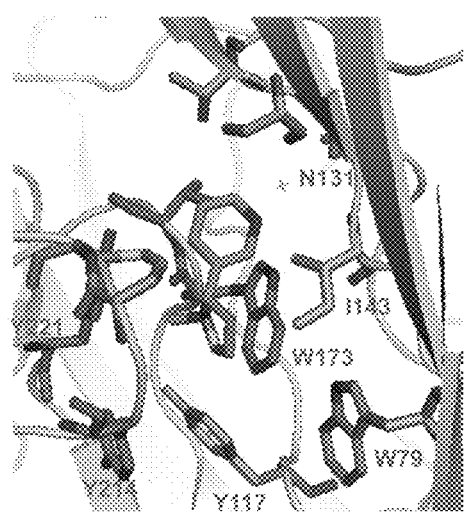
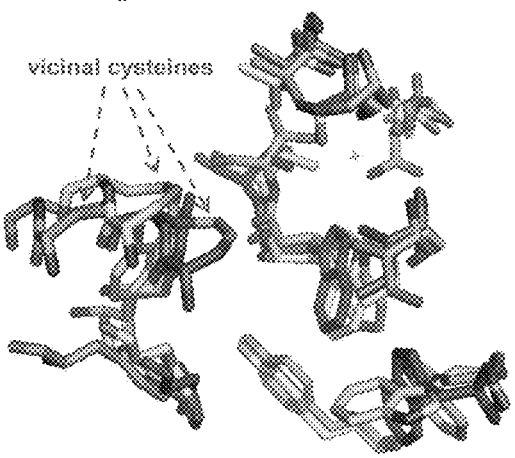
FIG. 2C  FIG. 2D

Lst-AChBP human α7 AChR chimera agonist-bound Asu-ACR-16 apo form of Asu-ACR-16

| 5-electron-withdrawing group substituted pyridine derivatives |
|---|

| 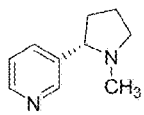 | 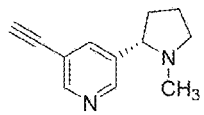 | 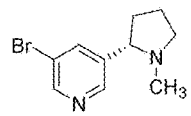 | 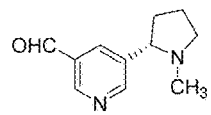 |
|---|---|---|---|
| (S)-nicotine | (S)-SIB 1508Y | (S)-5-bromonicotine | (S)-nicotine-5-carboxaldehyde |

| other pyridine ring substituted derivatives |
|---|

| 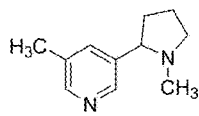 | 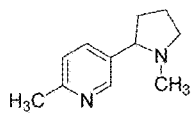 | 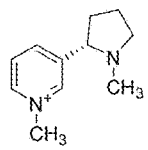 | 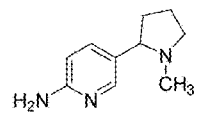 |
|---|---|---|---|
| 5-methylnicotine | 6-methylnicotine | (S)-1-methylnicotinium | 6-AN |

| pyrrolidine ring substituted derivatives |
|---|

| 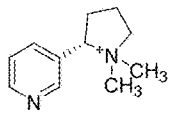 | 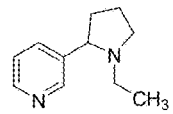 | 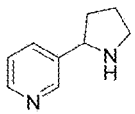 | 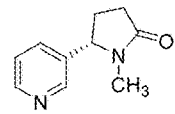 |
|---|---|---|---|
| (S)-1'-methylnicotinium | homonicotine | nornicotine | (S)-cotinine |

| piperidine ring derivatives |
|---|

| 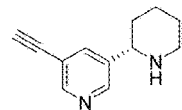 | 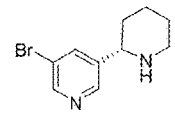 | 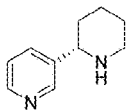 | 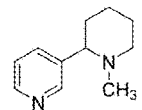 |
|---|---|---|---|
| (S)-5-ethynyl-anabasine | (S)-5-bromoanabasine | (S)-anabasine | N-methyl anabasine |

FIG. 4

(S)-5-ETHYNYL-ANABASINE, DERIVATIVES THEREOF, AND RELATED COMPOSITIONS AND METHODS OF MAKING AND USING

CROSS REFERENCE TO RELATED APPLICATIONS

This application claims priority to U.S. provisional patent application No. 62/424,496, which was filed Nov. 20, 2016, and which is incorporated herein by reference in its entirety.

STATEMENT REGARDING FEDERALLY SPONSORED RESEARCH OR DEVELOPMENT

This invention was made with government support under grant nos. R01AI047194 and R21AI121831 awarded by the National Institutes of Health. The government has certain rights in the invention.

TECHNICAL FIELD

The present disclosure relates to nicotine alkaloids, in particular (S)-5-ethynyl-anabasine and derivatives thereof, compositions comprising the same, and related methods of making and using the same, such as in the treatment of infection with a nematode parasite, such as an *Ascaris*.

BACKGROUND

Nematode parasites infect approximately two billion people worldwide. *Ascaris*, a genus of clade III nematode parasites, is a gastrointestinal roundworm that infects humans, pigs, and other animals worldwide (Taylor et al., Emerging Infectious Diseases 22(2): 339-340 (2016)). *Ascaris* has been estimated to cause more than 1.2 billion human infections (de Silva et al., Trends Parasitology 19(12): 547-551 (2003)).

With no effective vaccines and inadequate sanitation in many countries, the control of *Ascaris* infection mainly relies on the limited number of available anthelmintic drugs. Some of these drugs act on nicotinic acetylcholine receptors (nAChRs). The nAChRs are pentameric ligand-gated ion channels involved in synaptic transmission in the nervous systems of vertebrates and invertebrates (Taly et al., Nat Rev Drug Discov 8(9): 733-750 (2009)). The receptors also serve a paracrine function in non-excitable tissues (Proskocil et al., Endocrinology 145: 2498-2506 (2004)). The nAChRs are activated by the ligands acetylcholine (ACh), nicotine, and structurally related derivatives, which leads to the opening of their transmembrane ion-channels and flux of sodium, potassium, and sometimes calcium ions, across the membrane. The agonist-binding sites of nAChRs have been well-studied using a combination of photolabeling, mutagenesis, and electrophysiology (Arias, Neurochem Int 36(7): 595-645 (2000)).

Acetylcholine binding proteins (AChBPs) are homologs of the extracellular agonist-binding site domain of nAChRs and share 20-24% sequence identity with the extracellular domain of AChRs (Blum et al., PNAS USA 107(30): 13206-13211 (2010)). Co-crystallization of invertebrate acetylcholine binding proteins (AChBPs) and cholinergic ligands has increased understanding of ligand interactions with the receptors (Rucktooa et al., Biochemical pharmacology 78(7): 777-787 (2009); and Sixma and Smit, Annual Review of Biophysics and Biomolecular Structure 32: 311-334 (2003)). The agonist-binding site of nAChRs is at the interface between the principal subunit (an α subunit with vicinal cysteines) and the adjacent complementary subunit (without vicinal cysteines) in the extracellular domain (ECD). Five aromatic amino acids in the agonist-binding site are highly conserved in nAChRs and contribute to the cation-π interactions with the cationic nitrogen in the nAChR agonists (Dougherty, Accounts of Chemical Research 46(4): 885-893 (2013)). Another feature of nAChR agonists is the hydrogen bond acceptor, which is about 4-6 Å from the cationic nitrogen. Based on the high-resolution structures of AChBPs, the hydrogen bond acceptor in the agonist is stabilized by a water molecule, which interacts with the carbonyl or the amide backbones of two less conserved residues on loop E of the complementary subunit through three hydrogen bonding interactions (Van Arnam and Dougherty (2014), supra).

The nicotinic acetylcholine receptor subtype 16 from *Ascaris suum* (Asu-ACR-16) is a homopentameric receptor, which resembles vertebrate α7 nAChRs (Mongan et al., Protein science: a publication of the Protein Society 11(5): 1162-1171 (2002)). Asu-ACR-16 is widely distributed in *A. suum* tissues but its physiological function remains to be determined (Abongwa et al., British Journal of Pharmacology (2016) DOI: 10.1111/bph.13524; and Zheng et al., Int'l J for Parasitology: Drugs and Drug Resistance 6(1): 60-73 (2016)). Asu-ACR-16 is pharmacologically different from its host α7 nAChR and may be exploited as an anthelmintic drug target to counter resistance to cholinergic anthelmintics directed at other pharmacological types of nAChR (Holden-Dye et al., Parasitology Int'l 62(6): 606-615 (2013); and Zheng et al. (2016), supra).

The agonist-binding site of the Asu-ACR-16 can be predicted by homology modeling using a human α7 nAChR chimera as a structural template. The chimera shares 38% identity and 73% sequence similarity with Asu-ACR-16. Five conserved aromatic residues and two hydrogen bond-interacting residues have orientations very close to corresponding residues in other nAChRs (Zheng et al. (2016), supra).

The Asu-ACR-16 is sensitive to six nicotinic agonists, namely nicotine, acetylcholine (Ach), cytisine, 3-bromocytisine, epibatidine, and dimethyl-4-phenylpiperazinium iodide (DMPP), and insensitive to other cholinergic anthelmintic agonists (Abongwa et al. (2016), supra). All six agonists share the nicotinic pharmacophore, which is a cationic nitrogen separated by ~5 Å from a hydrogen bond acceptor.

There is an urgent need for new drugs, given that resistance in various nematodes has been reported following frequent use of anthelmintic drugs (Garcia et al., Anais da Academia Brasileira de Ciencias 88(1): 397-402 (2016)). It is an object of the present disclosure to provide novel nicotine alkaloids, in particular nicotine alkaloids that are effective agonists of nAchRs in nematode parasites. This and other objects, and advantages, of the present disclosure will become apparent from the detailed description provided herein. The nicotine alkaloids provided herein have the potential to circumvent drug resistance that has arisen following repeated treatment of nematode parasites with other classes of anthelmintic drugs and are a useful lead for anthelmintic drug development.

SUMMARY

The present disclosure provides the compound (S)-5-ethynyl-anabasine. Also provided is (S)-5-ethynyl-anabasine comprising a substitution of one or more ring hydrogens. Each substitution is a moiety independently selected from the group consisting of:

alkyl, cycloalkyl, hydroxyalkyl, alkenyl, alkynyl, aryl, alkylaryl, arylalkyl, aryloxyalkyl, heterocyclic, trifluoromethyl, halo, cyano, cyanomethyl, nitro, —S(O)R', —S(O)$_2$R', —S(O)$_2$NHR', —NR$_2$', —C(O)R'', —OR', —OR''', —NR''', —SR', —SR'''', and SiR'''', wherein R' is hydrogen, alkyl, cycloalkyl, alkenyl, alkynyl, aryl, alkylaryl, arylalkyl, heterocyclic, trifluoromethyl, halo, cyano, or nitro, wherein R'' is hydrogen, alkyl, alkoxy, alkylamino, alkenyl, alkynyl, aryl, aryloxy, arylamino, alkylaryl, arylalkyl, heterocyclic, or trifluoromethyl, wherein R''' is hydrogen, alkyl, cycloalkyl, alkenyl, alkynyl, aryl, alkylaryl, arylalkyl, aroyl, heterocyclic, acyl, trifluoromethyl, alkylsulfonyl, or arylsulfonyl, wherein, when the moiety is NR''', R''' and the N to which it is attached can form a 4-, 5-, 6-, or 7-membered ring, wherein R'''' is hydrogen, alkyl, alkenyl, alkynyl, aryl, alkylaryl, arylakyl, heterocyclic, or trifluoromethyl, wherein any of the aforementioned moieties can be substituted, and wherein the compound has acetylcholine receptor-modulating activity.

In view of the above, also provided is a composition comprising (i) an above-described compound and (ii) a carrier. The composition can further comprise one or more other compounds having acetylcholine receptor-modulating activity. Additionally or alternatively, the composition can further comprise one or more other compounds having ascaricidal and/or nematicidal activity.

Thus, a method of prophylactically or therapeutically treating an animal for infection with a pest, such as a nematode, in particular an *Ascaris*, is also provided. The method comprises administering to the animal a prophylactically or therapeutically effective amount of an above-described composition.

Further provided is a method of treating an animal in need of modulation of acetylcholine receptors. The method comprises administering to the animal an acetylcholine receptor-modulating amount of an above-described composition. The animal can have a disease or disorder affecting the central nervous system. The animal can suffer from depression. The animal can be a human with Alzheimer's disease.

Still further provided is a method of protecting a plant from a pest, such as a nematode, in particular an *Ascaris*. The method comprises contacting the plant with a pesticidal amount of an above-described composition.

A method of making (S)-5-ethynyl-anabasine is also provided. The method comprises:

(a) adding di-tert-butyl dicarbonate (Boc$_2$O) to a solution of (S)-anabasine and triethylamine (Et$_3$N) in tetrahydrofuran (THF) at around 0° C. to form a first reaction mixture, (b) diluting the first reaction mixture with water and extracting the diluted first reaction mixture with ethyl acetate (EtOAc) to provide a first crude product, (c) purifying the first crude product to give (S)-tert-butyl 2-(pyrin-3-yl)piperidine-1-carboxylate, (d) adding methanesulfonato(2-di-t-butylphosphino-2',4',6'-tri-i-propyl-1,1'-biphenyl)(2'-amino-1,1'-biphenyl-2-yl)palladium(II) (Pd(PPH$_3$)$_2$Cl$_2$), iodide (CuI), N,N-diisopropylethylamine (DIPEA), and trimethylsilylacetylene to (S)-tert-butyl 2-(pyrin-3-yl)piperidine-1-carboxylate in THF to form a second reaction mixture, (e) filtering the second reaction mixture, washing the filtered second reaction mixture with EtOAc, and concentrating and purifying the filtrate to give a second crude product, (f) adding trifluoroacetic acid (TFA) to a solution of the second crude product in dichloromethane (DCM), (g) removing all volatiles and purifying the second crude product, (h) adding K$_2$CO$_3$ to a solution of the second crude product in methanol, and (i) filtering, concentrating, and purifying the second crude product to give (S)-5-ethynyl-anabasine.

Also provided is a method of modifying (S)-5-ethynyl-anabasine. The method comprises independently substituting one or more ring hydrogens with a moiety selected from the group consisting of:

alkyl, cycloalkyl, hydroxyalkyl, alkenyl, alkynyl, aryl, alkylaryl, arylalkyl, aryloxyalkyl, heterocyclic, trifluoromethyl, halo, cyano, cyanomethyl, nitro, —S(O)R', —S(O)$_2$R', —S(O)$_2$NHR', —NR$_2$', —C(O)R'', —OR', —OR''', —NR''', —SR', —SR'''', and SiR'''', wherein R' is hydrogen, alkyl, cycloalkyl, alkenyl, alkynyl, aryl, alkylaryl, arylalkyl, heterocyclic, trifluoromethyl, halo, cyano, or nitro, wherein R'' is hydrogen, alkyl, alkoxy, alkylamino, alkenyl, alkynyl, aryl, aryloxy, arylamino, alkylaryl, arylalkyl, heterocyclic, or trifluoromethyl, wherein R''' is hydrogen, alkyl, cycloalkyl, alkenyl, alkynyl, aryl, alkylaryl, arylalkyl, aroyl, heterocyclic, acyl, trifluoromethyl, alkylsulfonyl, or arylsulfonyl, wherein, when the moiety is NR''', R''' and the N to which it is attached can form a 4-, 5-, 6-, or 7-membered ring, wherein R'''' is hydrogen, alkyl, alkenyl, alkynyl, aryl, alkylaryl, arylakyl, heterocyclic, or trifluoromethyl, wherein any of the aforementioned moieties can be substituted, and wherein the compound has acetylcholine receptor-modulating activity.

BRIEF DESCRIPTION OF FIGURES

FIG. 1A shows the amino acid sequence alignment of the extracellular domain (ECD) of Asu-ACR-16 (ECD-Asu-ACR-16; UniProtKB ID: F1KYJ9; [SEQ ID NO: 1]) and Lst-AChBP (SwissProt ID: P58154; [SEQ ID NO: 2]). Completely conserved residues are shown in red. Partially conserved residues are shown in yellow. Highly conserved residues in the ligand-binding site of the principal subunit are indicated with pink arrows. Variable residues in the ligand-binding site of the complementary subunit are indicated with purple arrows.

FIG. 1B shows the amino acid sequence alignment of the ECD of human α7 nAChR chimera (PDB code: 3SQ6; [SEQ ID NO: 3]) and its alignment with the ECD of human α7 nAChR (SwissProt ID: P36544; [SEQ ID NO: 4]). Completely conserved residues are shown in red. Partially conserved residues are shown in yellow. Highly conserved residues in the ligand-binding site of the principal subunit are indicated with pink arrows. Variable residues in the ligand-binding site of the complementary subunit are indicated with purple arrows.

FIG. 2A is a ribbon diagram of Lst-AChBP co-crystallized with nicotine (PDB code: 1UW6) as viewed with the membrane at the bottom. The principal subunit is highlighted by light pink. The complementary subunit is highlighted by light purple. Nicotine is shown in orange color.

Nicotine is bound in the five ligand-binding sites in the extracellular domain (ECD) of AChBP.

FIG. 2B is a close view of the AChBP ligand-binding site as viewed with the membrane at the bottom. The principal subunit is highlighted by pink. The complementary subunit is highlighted by light purple. Residues interacting with nicotine (orange) are represented as sticks ((+), pink; (−), purple). The water molecule is shown as a red dot.

FIG. 2C is a close view of the agonist-bound model of Asu-ACR-16 ligand-binding site as viewed with the membrane at the bottom. The principal subunit is highlighted by light pink. The complementary subunit is highlighted in light purple. The interacting residues are represented as sticks ((+), pink; (−), purple). The water molecule is shown as a red dot.

FIG. 2D shows superposition of residues in the agonist-binding site for the agonist-bound form (blue), the apo (no ligand) form (yellow), and the antagonist-bound form (green) of the Asu-ACR-16 models.

Figure 3A:
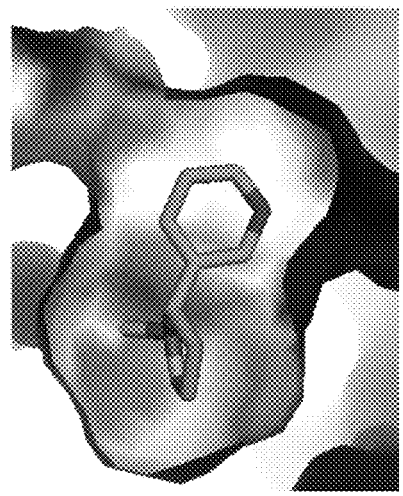

FIG. 3A shows the surface of the opened-up ligand-binding site of Lst-AChBP complexed with nicotine (PDB code: 1UW6). The oxygen-rich area is highlighted by red. The nitrogen-rich area is highlighted by blue. The carbon-rich area is highlighted by gray. Empty space was observed around the 5-pyridine ring of nicotine, which suggests the ligand-binding site is in favor of the linear functional group linking toward the 5-pyridine ring of nicotine. Little space is observed around the pyrrolidine ring of nicotine.

Figure 3B:
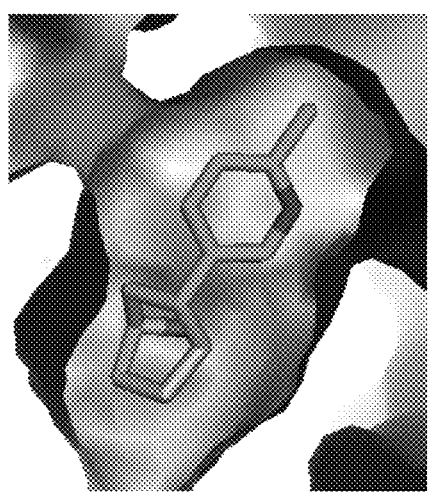

FIG. 3B shows the surface of the opened-up ligand-binding site of human α7 AChR chimera complexed with epibatidine (PDB code: 3SQ6) viewed from the same angle as FIG. 3A. The oxygen-rich area is highlighted by red. The nitrogen-rich area is highlighted by blue. The carbon-rich area is highlighted by pink. The chloride-rich area is highlighted by green. The azabicyclic ring N1 of epibatidine was superimposed with the pyrrolidine ring N2 of nicotine, while the pyridine ring N2 of epibatidine was superimposed with the pyridine ring N1 of nicotine.

Figure 3C:
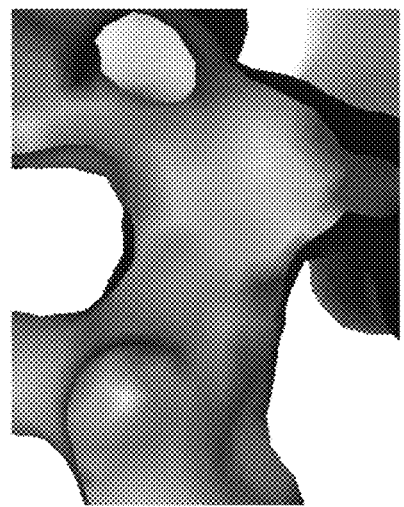

FIG. 3C shows the surface of the opened-up ligand-binding site of the agonist-bound Asu-ACR-16 model viewed from the same angle as FIG. 3A. The oxygen-rich area is highlighted by red. The nitrogen-rich area is highlighted by blue. The carbon-rich area is highlighted by cyan. Assuming the nicotine has the same binding position as in FIG. 3A with the agonist-bound Asu-ACR-16, empty space would be observed around the 5-pyridine ring and the pyrrolidine ring of nicotine, which would allow nicotinic derivatives with modifications at these positions to fit into the binding site.

Figure 3D:
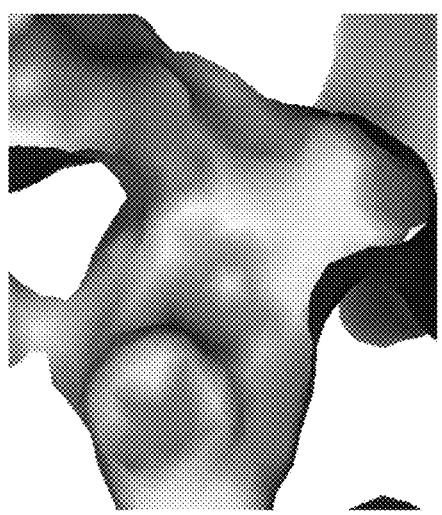

FIG. 3D shows the surface of the opened-up ligand-binding site of the apo form Asu-ACR-16 model viewed from the same angle as FIG. 3A. The oxygen-rich area is highlighted by red. The nitrogen-rich area is highlighted by blue. The carbon-rich area is highlighted by yellow. Assuming the nicotine has the same binding position as in FIG. 3A with the apo form Asu-ACR-16, empty space would be observed around the 5-pyridine ring and the pyrrolidine ring of nicotine, which would allow nicotinic derivatives with modifications at these positions to fit into the binding site.

FIG. 4 shows the chemical structures of (S)-nicotine and 15 derivatives.

Figure 5A:
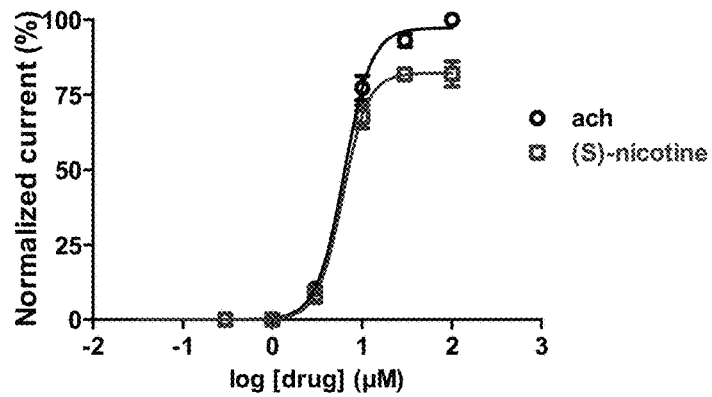

FIG. 5A shows the dose-response curves of ACh and (S)-nicotine with Asu-ACR-16 expressed in a frog oocyte.

Figure 5B:
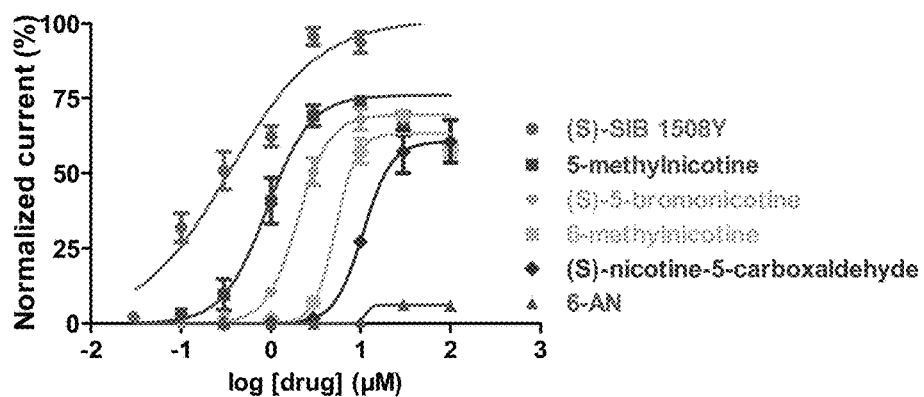

FIG. 5B shows the dose-response curves of pyridine ring-substituted derivatives of nicotine with Asu-ACR-16 expressed in a frog oocyte. The responses of 30 μM 5-methylnicotine and 100 μM 6-methylnicotine are shown but were not included for fitting the Hill equation to estimate $EC_{50}$, $n_H$, and $I_{max}$ because of their inhibitory effects at high concentrations.

Figure 5C:
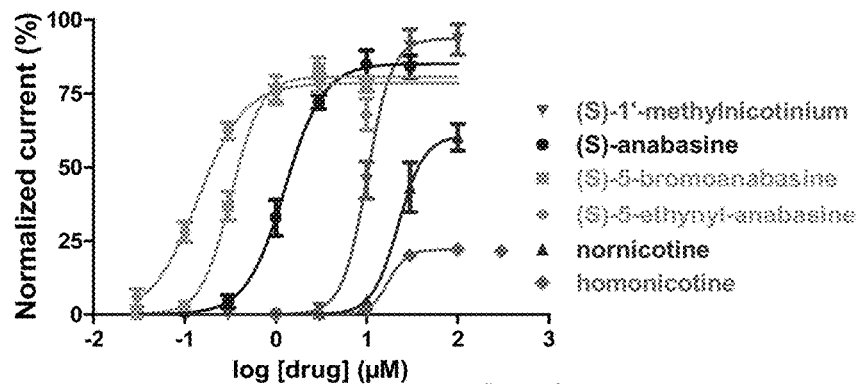

FIG. 5C shows the dose-response curves of pyrrolidine ring-substituted derivatives of nicotine with Asu-ACR-16 expressed in a frog oocyte. The response of 300 μM homonicotine is shown but was not included for fitting the Hill equation to estimate $EC_{50}$, $n_H$, and $I_{max}$ because of its inhibitory effect at high concentration.

Figure 6:
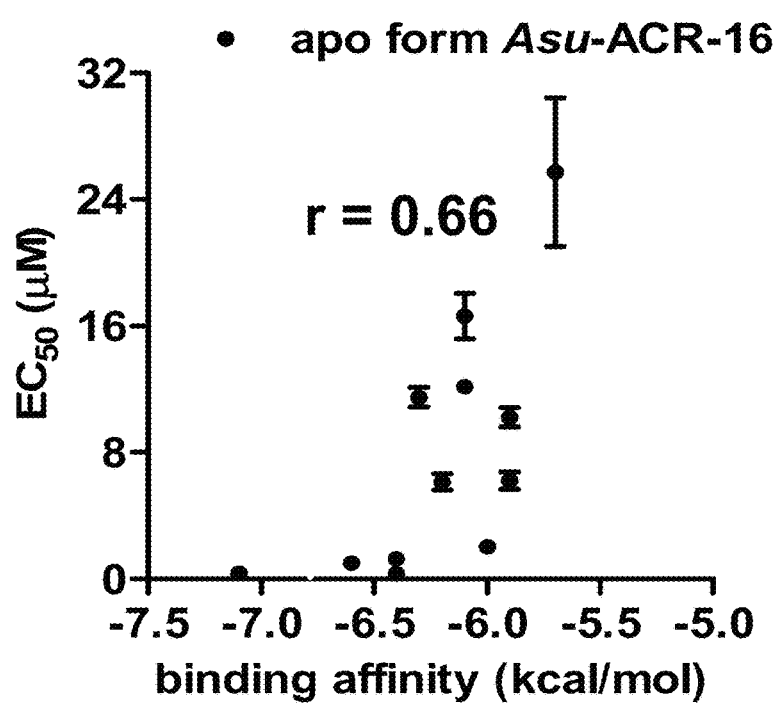

FIG. 6 shows correlations between binding affinities (kcal/mol) of each derivative in the apo form Asu-ACR-16 and $EC_{50}$ (μM), binding affinities (kcal/mol) for the selected nicotine derivatives. The correlation coefficient (r) was used for evaluating the linear regression between affinities and pharmacological parameters (r=0.66, P<0.05).

Figure 7A:
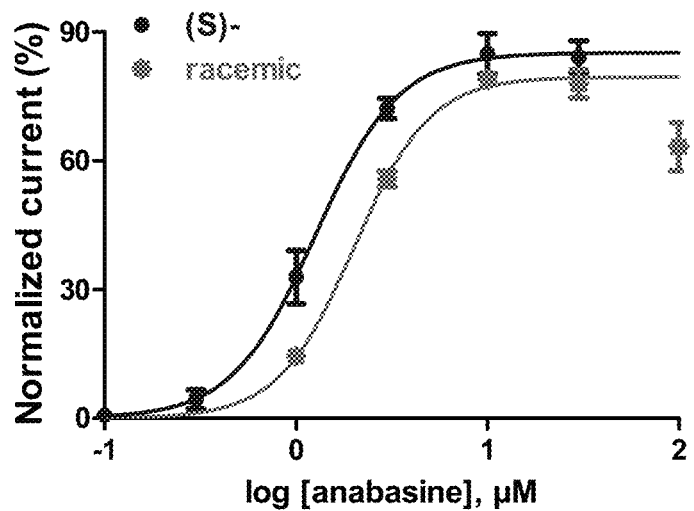

FIG. 7A shows the dose-response curves of (S)-anabasine (blue) and its racemic mixture (S, R)-anabasine (dark yellow) with Asu-ACR-16 expressed in a frog oocyte. The response of 100 μM (S, R)-anabasine is shown but not fitted into its stimulatory dose-response plot due to its inhibitory effect.

Figures 7B, 7C:
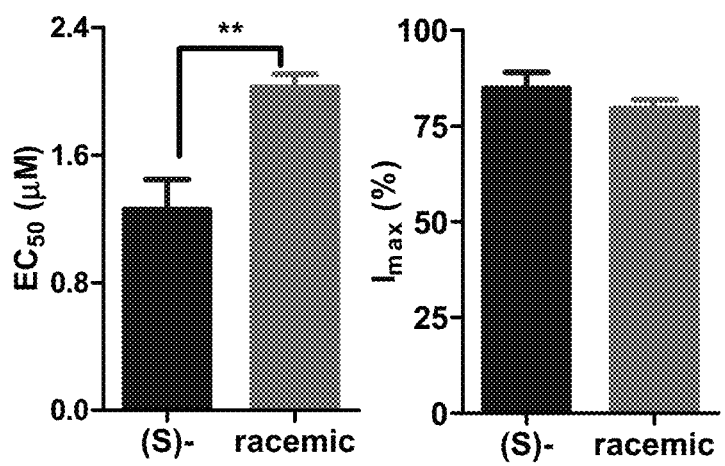

FIG. 7B is a bar chart showing the $EC_{50}$ (mean±S.E.M., μM) of (S)-anabasine and its racemic mixture for Asu-ACR-16 expressed in a frog oocyte using an unpaired student's t-test. P>0.05.

FIG. 7C is a bar chart showing the $I_{max}$ (mean±S.E.M., μM) of (S)-anabasine and its racemic mixture for Asu-ACR-16 expressed in a frog oocyte using an unpaired student's t-test. P>0.05.

Figure 8A:
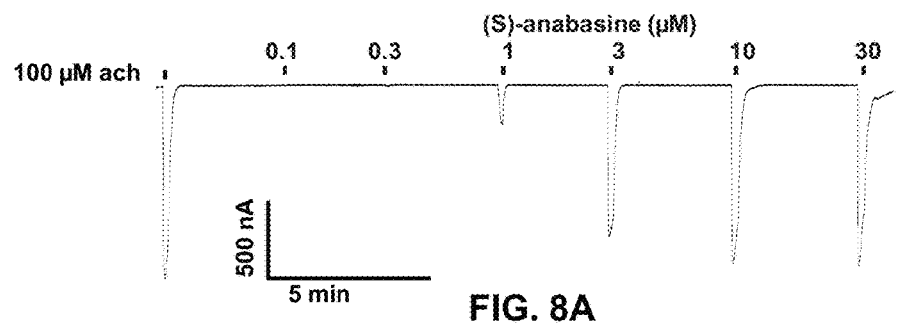

FIG. 8A shows a sample current recording trace for the dose-response relationship of (S)-anabasine with Asu-ACR-16 expressed in a frog oocyte.

Figure 8B:
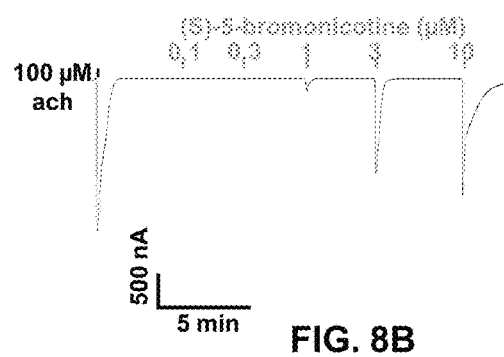

FIG. 8B shows a sample current recording trace for the dose-response relationship of (S)-5-bromonicotine with Asu-ACR-16 expressed in a frog oocyte.

Figure 8C:
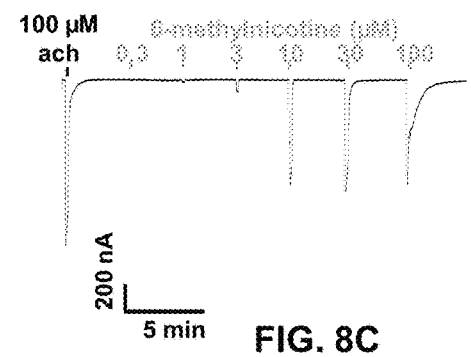

FIG. 8C shows a sample current recording trace for the dose-response relationship of 6-methylnicotine with Asu-ACR-16 expressed in a frog oocyte.

Figure 8D:
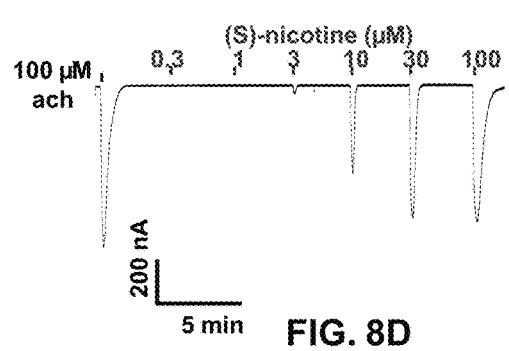

FIG. 8D shows a sample current recording trace for the dose-response relationship of (S)-nicotine with Asu-ACR-16 expressed in a frog oocyte.

Figure 8E:
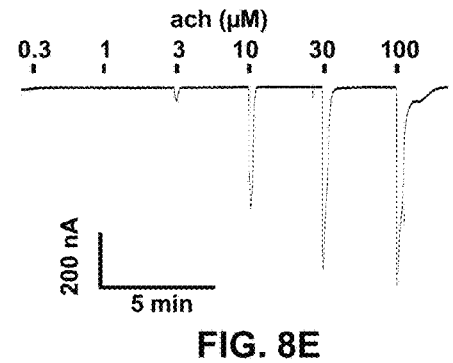

FIG. 8E shows a sample current recording trace for the dose-response relationship of ACh with Asu-ACR-16 expressed in a frog oocyte.

Figure 8F:
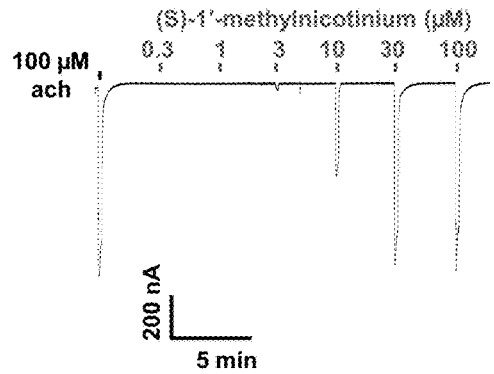

FIG. 8F shows a sample current recording trace for the dose-response relationship of (S)-1'-methylnicotinium with Asu-ACR-16 expressed in a frog oocyte.

Figure 8G:
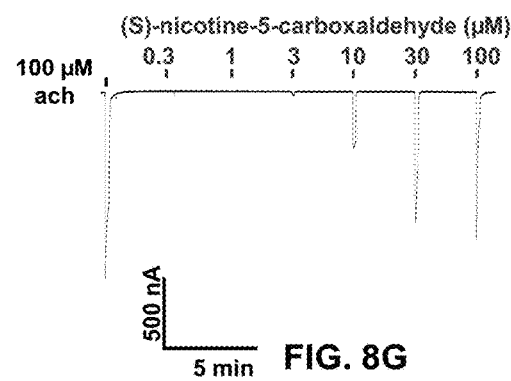

FIG. 8G shows a sample current recording trace for the dose-response relationship of (S)-nicotine-5-carboxaldehyde with Asu-ACR-16 expressed in a frog oocyte.

Figure 8H:
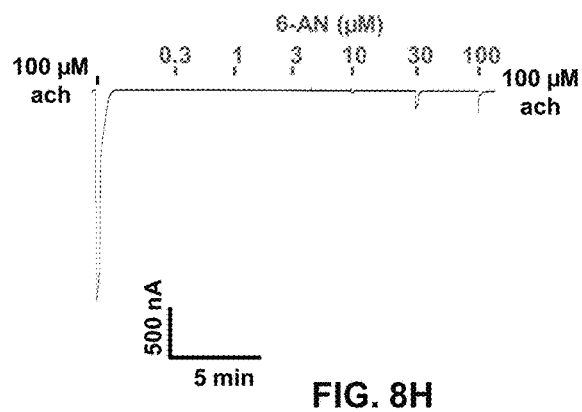

FIG. 8H shows a sample current recording trace for the dose-response relationship of 6-AN with Asu-ACR-16 expressed in a frog oocyte.

Figure 8I:
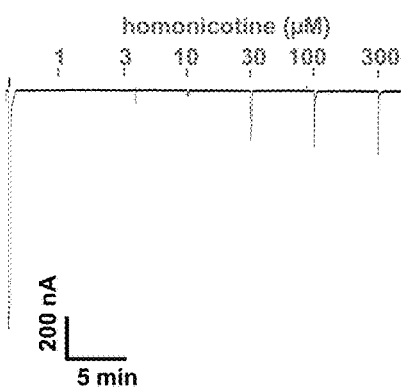

FIG. 8I shows a sample current recording trace for the dose-response relationship of homonicotine with Asu-ACR-16 expressed in a frog oocyte.

Figure 8J:
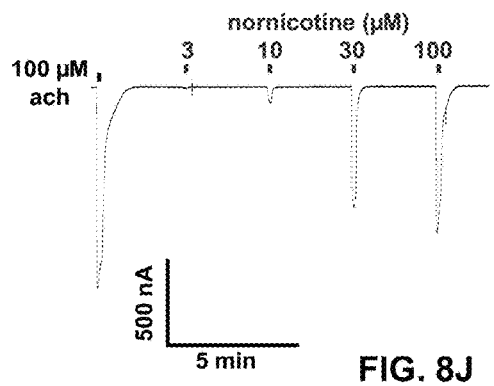

FIG. 8J shows a sample current recording trace for the dose-response relationship of nornicotine with Asu-ACR-16 expressed in a frog oocyte.

Figure 8K:
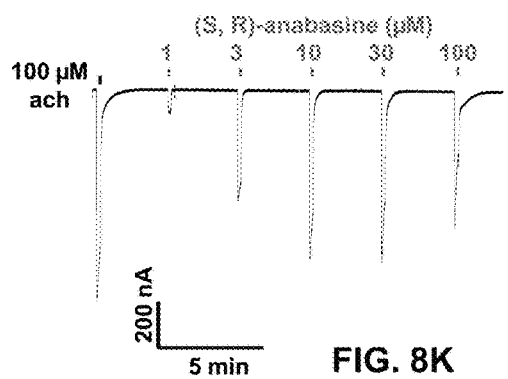

FIG. 8K shows a sample current recording trace for the dose-response relationship of (S, R)-anabasine with Asu-ACR-16 expressed in a frog oocyte.

Figure 9A:
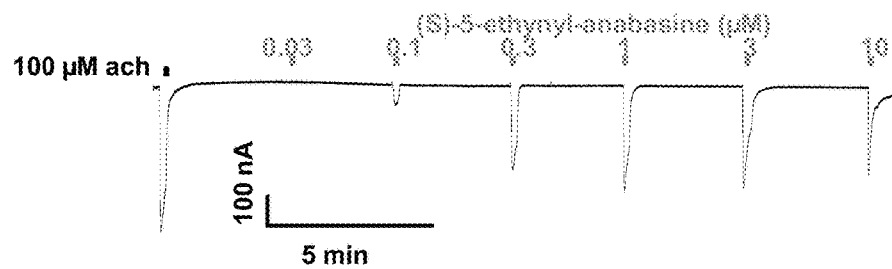

FIG. 9A shows a sample current recording trace for the dose-response relationship of (S)-5-ethynyl-anabasine with Asu-ACR-16 expressed in a frog oocyte.

Figure 9B:
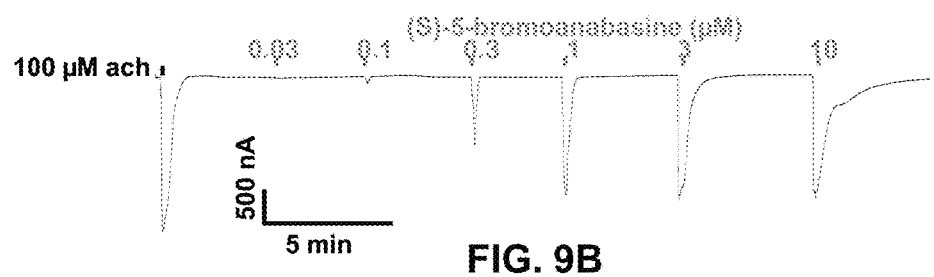

FIG. 9B shows a sample current recording trace for the dose-response relationship of (S)-5-bromoanabasine with Asu-ACR-16 expressed in a frog oocyte.

Figure 9C:
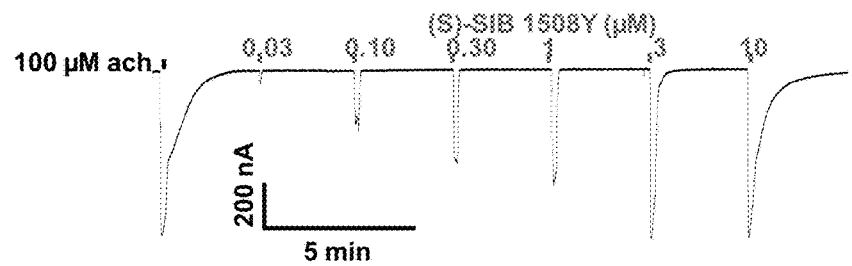

FIG. 9C shows a sample current recording trace for the dose-response relationship of (S)-SIB 1508Y with Asu-ACR-16 expressed in a frog oocyte.

Figure 9D:
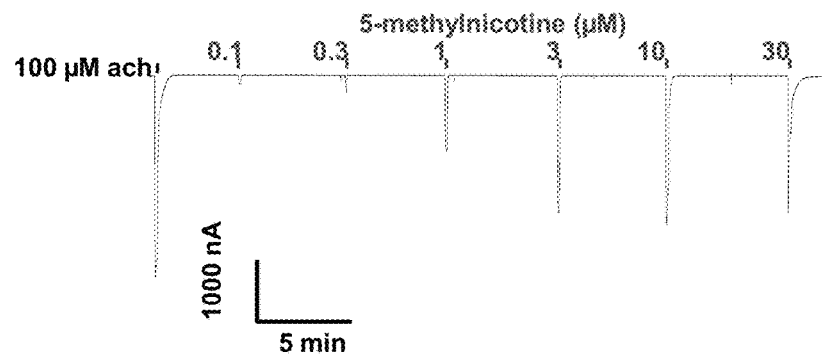

FIG. 9D shows a sample current recording trace for the dose-response relationship of 5-methylnicotine with Asu-ACR-16 expressed in a frog oocyte.

DETAILED DESCRIPTION

The present disclosure is predicated, at least in part, on the discovery of nicotine alkaloids that modulate nAChRs in nematode parasites, e.g., *Ascaris*, in particular the Asu-ACR-16 receptor. The compounds may act as agonists, partial agonists, antagonists, or allosteric modulators of AChRs, such as nicotinic AChRs (nAChRs) and muscarinic AChRs (mAChRs), in particular nAChRs.

In view of the above, provided is the compound (S)-5-ethynyl-anabasine. The compound can be modified, such as by substitution of one or more ring hydrogens. For example, one or more ring hydrogens can be substituted with a moiety that is independently selected from the group consisting of:

alkyl, cycloalkyl, hydroxyalkyl, alkenyl, alkynyl, aryl, alkylaryl, arylalkyl, aryloxyalkyl, heterocyclic, trifluoromethyl, halo, cyano, cyanomethyl, nitro, —S(O)R', —S(O)$_2$R', —S(O)$_2$NHR', —NR$_2$', —C(O)R'', —OR', —OR''', —NR''', —SR', —SR'''', and SiR'''', wherein R' is hydrogen, alkyl, cycloalkyl, alkenyl, alkynyl, aryl, alkylaryl, arylalkyl, heterocyclic, trifluoromethyl, halo, cyano, or nitro, wherein R'' is hydrogen, alkyl, alkoxy, alkylamino, alkenyl, alkynyl, aryl, aryloxy, arylamino, alkylaryl, arylalkyl, heterocyclic, or trifluoromethyl, wherein R''' is hydrogen, alkyl, cycloalkyl, alkenyl, alkynyl, aryl, alkylaryl, arylalkyl, aroyl, heterocyclic, acyl, trifluoromethyl, alkylsulfonyl, or arylsulfonyl, wherein, when the moiety is NR''', R''' and the N to which it is attached can form a 4-, 5-, 6-, or 7-membered ring, wherein R'''' is hydrogen, alkyl, alkenyl, alkynyl, aryl, alkylaryl, arylakyl, heterocyclic, or trifluoromethyl, and wherein any of the aforementioned moieties can be substituted. Desirably, the modified compound has acetylcholine-receptor modulating activity (i.e., it can modulate AChR, in particular nAChR, such as nAChR from a parasite, such as a nematode, in particular *Ascaris*).

If desired, any of the above compounds can be converted into an acid-addition salt, such as by reaction with a suitable inorganic/organic acid, in accordance with methods known in the art. Examples of such salts include acetate, bisulfate, benzoate, borate, citrate, fumarate, hydrobromide, hydrochloride, lactate, laurate, maleate, methanesulfonate, napsylate, oxalate, oleate, phosphate, succinate, sulfate, tartrate, tosylate, and valerate. Examples of salts for agricultural and horticultural use include salts formed by using amines, alkali metal bases, alkaline earth metal bases, quaternary ammonium bases, and metal chelates, including salts of di- and trivalent transition metal ions such as $Al^{+3}$, $Ba^{+2}$, $Ca^{+2}$, $Co^{+2}$, $Cu^{+2}$, $Fe^{+3}$, $Ni^{+2}$, $Ti^{+3}$, $Zn^{+2}$, and $[CH_3(CH_2)_7]_3N$. Examples of amines for ammonium salt formation include ammonia, primary, secondary and tertiary $C_{1-18}$ alkylamines, $C_{1-4}$ hydroxylalkylamines, $C_{2-4}$ alkoxylalkylamines, heterocyclic amines, and primary aryl amines. The above compounds also can be prepared as salt derivatives, solvates, ester derivatives, and the like (see, e.g., col. 101, line 6, through col. 102, line 4, of U.S. Pat. No. 9,445,594, which is specifically incorporated herein by reference for its teachings regarding same; see the corresponding section of U.S. Pat. No. 9,445,597, which is also specifically incorporated by reference for its teachings regarding same).

Activity of the above compounds for AChRs, such as nAChRs and mAChRs, in particular nAChRs, can be demonstrated in accordance with methods known in the art. Examples of such methods include competitive radioligand binding experiments, such as when a test compound displaces a radiolabeled ligand (e.g., nicotine) from a binding site. The binding of a compound to an AChR can be evaluated as a functional response. For example, the activity of the compound can be evaluated by employing a functional assay based on a recombinant nAChR expression system. Compounds also can be evaluated for their ability to modulate the release of a neurotransmitter from a receptor (e.g., in a brain slice, such as a rat brain slice). Compounds also can be evaluated by way of behavioral studies employing animal models of various CNS, autonomic, and cardiovascular disorders as known in the art.

In view of the above, also provided is a composition comprising (i) an above-described compound and (ii) a carrier. The composition can be administered by any suitable route as known in the art. When the composition is to be administered to an animal, in particular a human, the carrier should be pharmaceutically acceptable. Pharmaceutically acceptable carriers include those that are suitable for oral, intravenous, transcutaneous, intra-cutaneous, subcutaneous, intramuscular, and nasal administration. The composition can be in the form of a tablet, a capsule, a dispersible powder, granules, a syrup, an elixir, an aqueous or non-aqueous solution, suspension, or emulsion, a cream, a lotion, or a patch. Examples of non-aqueous solvents or vehicles include propylene glycol, polyethylene glycol, gelatin, organic esters, and vegetable oils. Adjuvants, such as preservatives, wetting agent, emulsifiers, and dispersants, can be added. For formulations suitable for agricultural/horticultural application, see, e.g., col. 113, line 12, through col. 117, line 52, of U.S. Pat. No. 9,445,594, which is specifically incorporated herein by reference for its teachings regarding same; also discussed therein are methods of nematode control at, for example, col. 122, line 5, through col. 124, last line, which section is also incorporated herein by reference for its teachings regarding same (see the corresponding sections of U.S. Pat. No. 9,445,597, which is also specifically incorporated by reference for its teachings regarding same).

The compound should be present in the composition in an amount sufficient to modulate acetylcholine receptor activity. For example, such an amount can be in the range of from about 1 mg to about 100 mg per kg of body weight of an animal, such as a human, to which the composition is being administered. The amount should be high enough to impart a beneficial effect on the recipient. Typically, a beneficial effect can be realized when levels are in the range from about 0.001 to about 100 mg/kg/day, such as from about 0.05 to about 10 mg/kg/day. For agricultural/horticultural applications, an application rate of between about 10 g a.i./hectare (g/ha) to about 7,500 g/ha can be used, such as between about 50 g/ha and 5,000 g/ha.

The composition can further comprise one or more other compounds having acetylcholine receptor-modulating activity. Such compounds can have ascaricidal and/or nematicidal activity. Compounds having acetylcholine receptor-modulating activity, such as ascaricidal and/or nematicidal activity, are known in the art. Examples include those compounds set forth in FIG. 4. More specific examples include nicotine, nornicotine, anabasine, N-methyl anabasine, anabaseine, anatabine, N-methyl-2-oxoanabasine, myosmine, and cotinine. The selection of one or more other compounds will depend, at least in part, upon whether a plant or an animal is being treated, the purpose of the treatment, and whether the treatment is prophylactic or therapeutic. In the context of agricultural/horticultural application, it can be desirable to include an insecticide, an ascaricide, a nematicide, a fungicide, and/or an herbicide in the composition (see, e.g., col. 10, line 56, through col. 12, line 20, and col. 13, line 29, through col. 14, line 12, of U.S. Pat. No. 7,973,083, which is specifically incorporated herein by reference for its teachings regarding same; and col. 102, line 5, through col. 112, line 3, of U.S. Pat. No. 9,445,594, which is specifically incorporated herein by reference for its teachings regarding same, and the corresponding sections of U.S. Pat. No. 9,445,597, which is also specifically incorporated by reference for its teachings regarding same).

Thus, in view of the above, a method of prophylactically or therapeutically treating an animal for infection with a pest is also provided. The method comprises administering to the animal a prophylactically or therapeutically effective amount of an above-described composition. The pest can be a nematode, such as an *Ascaris*.

Also in view of the above, a method of treating an animal in need of modulation of acetylcholine receptors is provided. The method comprises administering to the animal an acetylcholine receptor-modulating amount of an above-described composition. Indications for treatment of an animal with a modulator of an AChR include, for example, a disease of the central nervous system (CNS), such as Alzheimer's disease, a disorder involving memory loss and/or dementia, cognitive dysfunction, a disorder affecting extrapyramidal motor function, a mood or emotional disorder, substance abuse, a neuroendocrine disorder, dysregulation of food intake, a disorder of nociception and pain control, an autonomic disorder, pheochromocytoma, and a cardiovascular dysfunction. The dementia can be associated with AIDS. Cognitive dysfunction can affect attention, focus, and/or concentration. Examples of disorders affecting extrapyramidal motor function include Parkinson's disease, progressive supramuscular palsy, Huntington's disease, Gilles de la Tourette syndrome, and tardive dyskinesia. Example of mood and emotional disorders include depression, panic, anxiety, and psychosis. Substance abuse can include withdrawal and substitution therapy. Dysregulation of food intake can involve bulimia or anorexia. Autonomic disorders can include dysfunction of gastrointestinal motility and function, such as inflammatory bowel disease, irritable bowel syndrome, diarrhea, constipation, gastric acid secretion, and ulcers. Cardiovascular dysfunction can include hypertension and cardiac arrhythmias.

In general, (S)-5-ethynyl-anabasine (or a derivative thereof as described herein) can be used to assess the pharmacological profile of AChRs, in particular nAChRs, such as the human α-7 receptors. By comparing the effects of (S)-5-ethynyl-anabasine (or a derivative thereof as described herein) with other active compounds, whether agonists, partial agonists, antagonists, or partial antagonists, the roles of different receptor types can be identified and evaluated.

In view of the above, (S)-5-ethynyl-anabasine (or a derivative thereof as described herein) can be used as an aid in the diagnosis of loss of function of α-7 receptors, such as loss of function associated with a memory loss disorder, such as Alzheimer's disease, in a human. The compound can be administered to a patient by any suitable route, such as intravenously. The effect of the administration of the compound can be evaluated, for example, by assessing impact on memory through the use of memory function tests as well as by electroencephalogram (EEG) and brain imaging tests. By comparing the effect of the administration of (S)-5-ethynyl-anabasine with other compounds, such as selective cholinergic agonists, the type of receptor loss associated with a given memory loss disorder can be determined.

Similarly, (S)-5-ethynyl-anabasine (or a derivative thereof as described herein) can be used to assess anthelmintic sensitivity in a parasite, such as a nematode. The compound can be particularly useful for assessing anthelmintic sensitivity in *Ascaris*.

Further provided is a method of protecting a plant from a pest is provided. The method comprises contacting the plant with a pesticidal amount of an above-described composition. The pest can be a nematode, such as an *Ascaris*. The plant can be contacted with the composition using any suitable method as known in the art (see, e.g., discussion of field application rates above).

A method of making (S)-5-ethynyl-anabasine is also provided. In an embodiment the method comprises adding di-tert-butyl dicarbonate ($Boc_2O$) to a solution of (S)-anabasine and triethylamine ($Et_3N$) in an aprotic solvent, such as tetrahydrofuran (THF), at around 0° C. to form a first reaction mixture. Other examples of aprotic solvents include diethyl ether, tert-butyl methyl ether, 1,2-dimethoxyethane, and toluene; THF can be preferred. While the reaction can be carried out over a range of temperatures, it is preferred that the reaction is carried out at around 0° C., such as at 0° C. The first reaction mixture can be extracted, such as with ethyl acetate (EtOAc), to provide a first crude product. The first reaction mixture can be diluted with water prior to extraction. The first crude product can be purified to give (S)-tert-butyl 2-(pyrin-3-yl)piperidine-1-carboxylate. A second reaction mixture can be formed by adding methanesulfonato(2-di-t-butylphosphino-2',4',6'-tri-i-propyl-1,1'-biphenyl)(2'-amino-1, 1'-biphenyl-2-yl)palladium(II) ($Pd(PPH_3)_2Cl_2$), iodide (CuI), N,N-diisopropylethylamine (DIPEA), and trimethylsilylacetylene, for example, to (S)-tert-butyl 2-(pyrin-3-yl)piperidine-1-carboxylate, such as (S)-tert-butyl 2-(pyrin-3-yl)piperidine-1-carboxylate in THF. The second reaction mixture can be processed to give a second crude product. For example, the second reaction mixture can be filtered, washed (e.g., with EtOAc), concentrated, and purified. A solution of the second crude product, such as the second crude product in dichloromethane (DCM), can be mixed with a strong acid, such as trifluoroacetic acid (TFA). Other examples of strong acids include hydrochloric acid, hydrobromic acid, and sulfuric acid; TFA can be preferred. Afterwards, volatiles can be removed, and the second crude product can be purified. A subsequent solution of the second crude product, such as the second crude product in methanol, can be mixed with $K_2CO_3$. Then, the second crude product can be processed, e.g., filtered, concentrated, and purified, to give (S)-5-ethynyl-anabasine. See the "Examples" herein, Beng et al., JACS 13(3): 394-397 (2011) (specifically incorporated herein by reference), and Liskey et al., JACS 132: 11389-11391 (2010) (specifically incorporated herein by reference).

Also in view of the above, a method of modifying (S)-5-ethynyl-anabasine is provided. The method comprises independently substituting one or more hydrogens with a moiety selected from the group consisting of:

alkyl, cycloalkyl, hydroxyalkyl, alkenyl, alkynyl, aryl, alkylaryl, arylalkyl, aryloxyalkyl, heterocyclic, trifluoromethyl, halo, cyano, cyanomethyl, nitro, —S(O)R', —S(O)$_2$R', —S(O)$_2$NHR', —NR$_2$', —C(O)R", —OR', —OR''', —NR'''', —SR', —SR'''', and SiR'''', wherein R' is hydrogen, alkyl, cycloalkyl, alkenyl, alkynyl, aryl, alkylaryl, arylalkyl, heterocyclic, trifluoromethyl, halo, cyano, or nitro, wherein R''' is hydrogen, alkyl, alkoxy, alkylamino, alkenyl, alkynyl, aryl, aryloxy, arylamino, alkylaryl, arylalkyl, heterocyclic, or trifluoromethyl, wherein R'''' is hydrogen, alkyl, cycloalkyl, alkenyl, alkynyl, aryl, alkylaryl, arylalkyl, aroyl, heterocyclic, acyl, trifluoromethyl, alkylsulfonyl, or arylsulfonyl, wherein, when the moiety is NR''', R'''' and the N to which it is attached can form a 4-, 5-, 6-, or 7-membered ring, wherein R'''' is hydrogen, alkyl, alkenyl, alkynyl, aryl, alkylaryl, arylakyl, heterocyclic, or trifluoromethyl, and wherein any of the aforementioned moieties can be substituted. Desirably, the modified compound has acetylcholine receptor-modulating activity (i.e., it can modulate AChR, in particular nAChR, such as nAChR from a parasite, such as a nematode, in particular *Ascaris*).

Other well-known synthetic chemistry techniques can be used. The literature is replete with methodologies useful for the preparation of anabasinic and nicotinic nuclei, which then can be modified to introduce moieties as set forth above. Purification techniques are also well-known and include, for example, chromatography, recrystallization, and distillation.

Compounds can contain one or more chiral centers and can exist as racemic mixtures. It can be desirable to carry out stereo-selective synthesis and/or to subject the compound to appropriate purification steps so as to produce substantially, optically pure materials. (S)-5-ethynyl-anabasine is an example of such a compound. Suitable stereo-selective synthetic procedures for producing optically pure materials are known in the art, as are procedures for purifying racemic mixtures into optically pure fractions. Similarly, methods of separating enantiomers of a racemic mixture are well-known and include, for example, chromatography utilizing a chiral stationary phase, such as chiral gas chromatography, chiral medium performance liquid chromatography, and chiral high performance liquid chromatography. See, for example, methods described in U.S. Pat. No. 5,677,459, in particular columns 8-18 and the "Examples," which is hereby incorporated by reference for its teachings regarding same; also incorporated by reference are corresponding sections in U.S. Pat. Nos. 5,703,100; 5,705,512; 5,723,477; and 5,594,011.

EXAMPLES

The following examples serve to illustrate the present invention. The examples are not intended to limit the scope of the claimed invention in any way.

Example 1

This example describes homology modeling and docking.

The Asu-ACR-16 sequence is available in the UniProtKB database under the accession number F1KYJ9 (Wang et al., Genome Research 21(9): 1462-1477 (2011)). It is reproduced here as [SEQ ID NO: 1] (see FIG. 1A). Three crystal structures of the human α7 nAChR chimera co-crystallized with ligands having different modes of action were used as templates to build three different bound-form models of the ECD of Asu-ACR-16 (ECD-Asu-ACR-16) (Table 1, which provides structural information for the ECD-Asu-ACR-16 and two of its homologous proteins, i.e., human α7 nAChR chimera and Lst-AChBP) (Huang et al., The Biochemical Journal 454(2): 303-310 (2013); Li et al., Nature Neuroscience 14(10): 1253-1259 (2011); and Zheng et al. (2016), supra). The smiles strings of nicotine derivatives were obtained from ZINC (http:// followed by zinc.docking.org/search/structure) and converted to PDBQT format. Docking of these ligands was performed at the orthosteric ligand-binding sites of agonist-bound, apo (no ligand), and antagonist-bound forms of the ECD-Asu-ACR-16 models using AutoDock Vina Software (Trott and Olson, J Comput Chem 31(2): 455-461 (2010); and Zheng et al. (2016), supra).

TABLE 1

| Protein | Organism | PDB Code | Resolution (Å) | Ligand | Pharmacology |
|---|---|---|---|---|---|
| ECD-ACR-16 | *Ascaris suum* | | | | |
| A7 nAChR | *Homo sapiens* + | 3SQ6 | 2.8 | epibatidine | agonist |
| chimera | *Lymnaea stagnalis* | 3SQ9 | 3.1 | none | none |
| | | 4HQP | 3.51 | α-bungarotoxin | antagonist |
| AChBP | *Lymnaea stagnalis* | 1UW6 | 2.2 | nicotine | agonist |

*Lymnaea stagnalis* acetylcholine binding protein (Lst-AChBP; PDB code: 1UW6; [SEQ ID NO: 2] in FIG. 1A) (Celie et al., Neuron 41(6): 907-914 (2004)) shows 23.33% sequence identity and 64.29% sequence similarity to ECD-Asu-ACR-16 (see FIG. 1A) and is the only crystal structure of a protein homologous to Asu-ACR-16 co-crystallized with nicotine to date. The ligand-binding site for agonist is at the interface between the principal side and the complementary side in two adjacent subunits of nAChRs (Li et al. (2011), supra; and Rucktooa et al., The Journal of Biological Chemistry 287(28): 23283-23293 (2012)).

Nicotine adopts the same binding pose in all five ligand-binding sites in the Lst-AChBP pentamer (see FIG. 2A). The pyrrolidine ring of nicotine is oriented toward the basal side of the binding site on the principal subunit, whereas the pyridine ring faces the apical side on the complementary subunit. The protonated nitrogen (N2) in the pyrrolidine ring of nicotine is involved in cation-π interactions with five aromatic side chains of residues in the binding site (principal subunit: Y89, W143, Y185, and Y192; complementary subunit: W53) (FIG. 2B). The N2 is also hydrogen-bonded to the hydroxyl moiety of Y89 and the W143 carbonyl backbone. Hydrophobic interactions from disulfide-bonded C187 and C188 on loop C stabilize nicotine in the binding pocket. The pyridine ring nitrogen of nicotine (Ni) is hydrogen-bonded to a water molecule, which is stabilized by the carbonyl backbone of L102 and the M114 amide backbone of the complementary subunit (FIG. 2B) (Celie et al. (2004), supra; and Van Arnam and Dougherty, J Med Chem 57(15): 6289-6300 (2014)).

FIG. 2C shows the ligand-binding site of the agonist-bound Asu-ACR-16 dimer viewed from the same angle as FIG. 2B. The residues involved in the binding site were highlighted in FIG. 2C and indicated in FIG. 1A by arrows. The interacting residues in the binding site of the agonist-bound Asu-ACR-16 model share similar orientations with those in the binding site of Lst-AchBP. The hydrophobic, hydrogen-bond, and van der Waals contacts between nicotine and AChBP were, therefore, predicted in Asu-ACR-16. Y117, W173, Y214, Y221 from the principal subunit and W79 from the complementary subunit constitute the aromatic cage, which makes a cation-π interaction with a protonated tertiary amine or a tetra-methyl ammonium salt of nicotine or its derivatives. The hydroxyl moiety of Y117 and the W173 carbonyl backbone are hydrogen-bonded to the protonated tertiary amino or ammonium of the ligand. The carbonyl backbone of N131 and the I143 amide backbone from the complementary face have a water-mediated, hydrogen bond with the pyridine ring N1 of the ligand.

Structural superimposition of the binding-site residues among three different bound forms of Asu-ACR-16 show details of conformational changes of residues when the agonist is in the binding pocket of the receptor. Of particular note is the inward movement of vicinal cysteines toward pyrrolidine N2 of nicotine. The antagonist-bound model has less steric hindrance in the open receptor binding site (FIG. 2D) (Huang et al. (2013), supra).

Figures 1A, 1B:
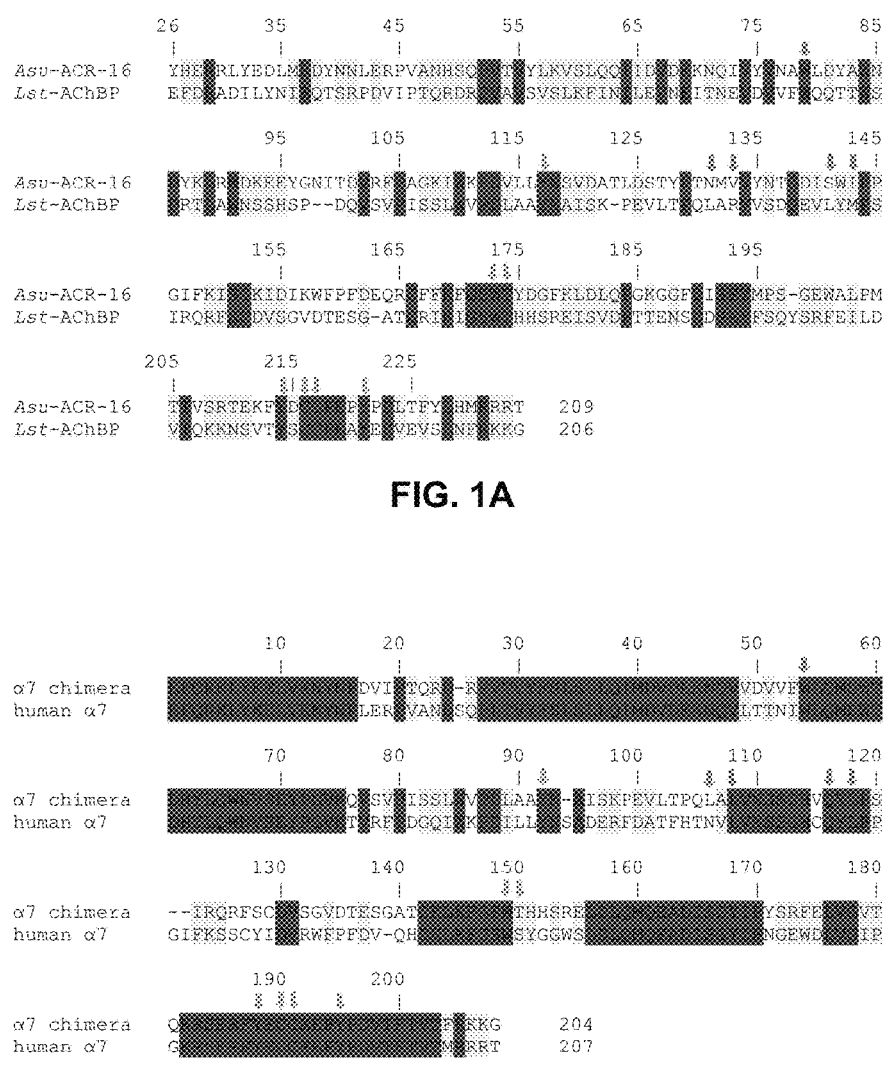

The human α7 nAChR chimera (PDB code: 3SQ6) (Li et al. (2011), supra) shows 62.98% sequence identity and 80.29% sequence similarity with the extracellular domain of human α7 nAChR (UniProtKB accession no. P36544). The residues constituting the ligand-binding site are highly conserved between the human α7 nAChR chimera ([SEQ ID NO: 3]; FIG. 1B) and the human α7 nAChR ([SEQ ID NO: 4]; FIG. 1B). The crystal structure of the human α7 nAChR chimera co-crystallized with epibatidine could be used to study the binding of agonist-bound human α7 nAChR. Comparison of the binding sites in Lst-AChBP (FIG. 3A), the human α7 nAChR chimera (FIG. 3B), the agonist-bound Asu-ACR-16 (FIG. 3C) and the apo form of Asu-ACR-16 (FIG. 3D) reveals that the 5-substituted pyridine derivatives of nicotine will be favorable for the binding site of the ECD-Asu-ACR-16, but not for the human α7 nAChR. The dotted arrows in FIG. 3D mark the likely orientation of the function group toward the 5-pyridine moiety of nicotine.

The binding affinities of the selected nicotine derivatives were calculated for ligands docking into the agonist-binding site in the agonist-bound form, the apo (no ligand) form, and the antagonist-bound form ECD-Asu-ACR-16 models. The relationship between the binding affinities and the observed values of the expressed receptors for the $EC_{50}$ (μM) of the nicotine derivatives. There was a positive correlation (+0.66) between the binding affinity and the $EC_{50}$ of the apo form model ($P<0.05$; FIG. 6). The correlation with the agonist bound Asu-ACR-16 (0.36) and the antagonist bound Asu-ACR-16 (0.46) were smaller and did not reach statistical significant ($P>0.05$). The highest correlation with the apo form suggests that this model is more likely to predict the potency of unknown agonists than the agonist-bound receptor or the antagonist-bound receptor.

The potency ($EC_{50}$) of the selected nicotinic alkaloids (see Example 10) correlated more with the binding affinity in the apo model of Asu-ACR-16 than binding affinity in the agonist-bound model or the antagonist-bound model of Asu-ACR-16. This appears to be due to the different conformational changes of vicinal cysteines or the opened-up orientation of W79 in the agonist-bound and the antagonist-bound models of Asu-ACR-16, which reduce the cation-π interaction between W79 and nicotine N2 (Blum et al. (2010), supra; Van Arnam and Dougherty (2014), supra). The statistical correlation between the predicted ligand binding affinities in the apo model of Asu-ACR-16 and their corresponding potencies ($EC_{50}$) suggests that the apo model would be more helpful than the other models to search for potent agonists by docking.

Example 2

This example describes the effect of substitutions of the pyridine moiety of nicotine.

A methyl group was added to the 5-, 6-, or N-pyridine moiety, and an amino group was added to the 6-pyridine moiety of nicotine. Methylnicotine was the most potent agonist, 6-methylnicotine was slightly less potent, and 6-AN showed little agonist activity.

The electron-donating group of the methyl or the amino at the 5- or 6-pyrine increases the electronegativity and alkalinity of the pyridine N1 and stabilizes the water-mediated hydrogen bond with the carbonyl backbone of N131 and the I143 amide backbone from the complementary subunit of the receptor. The long pair of electrons on the pyridine Ni of (S)-1-methylnicotinium is replaced by the methyl group. Thus, N1 cannot make a hydrogen bond with the carbonyl backbone of N131 and the I143 amide backbone of the receptor, which reduces the intrinsic activity of N-pyridine-substituted derivatives.

Given that the electron-donating groups substituting at the 5-pyridine of nicotine were found to have the highest potency as agonists, the electron-withdrawing groups of acetylene, bromine or aldehyde derivatives were substituted at the 5-pyridine of nicotine. (S)-SIB 1508 was the most potent, while (S)-5-bromonicotine and (S)-nicotine-5-carboxaldehyde were less potent. The extra cavity in the binding site of the Asu-ACR16 agonist-bound model and apo model can accommodate the linear acetylene substituent or the globular bromine atom at the 5-pyridine moiety of nicotine, allowing the ligands to extend into unoccupied space (FIG. 3C and FIG. 3D, top left quadrants of the binding pocket). The bent structure of aldehyde may be less favored in the binding pocket.

Example 3

This example describes the effect of substitutions of the pyrrolidine moiety of nicotine.

A methyl or ethyl group was added to the N-pyrrolidine moiety, and a ketone group was added to the 5'-pyrrolidine moiety of nicotine. The additional methyl group linked to the pyrrolidine N2 of (S)-1'-methylnicotinium produces a quaternary ammonium, which increases the cation-π interaction with the five aromatic residues from the ACR-16 receptor but increases the steric hindrance around the pyrrolidine N2 making the compound stereochemically unfavorable. The increased steric hindrance due to the ethyl group at pyrrolidine N2 of homonicotine may be the reason for its reduced agonist potency. The secondary amine of nornicotine reduces the alkalinity and the probability of making a cation-π interaction with the receptor.

The conjugative effect of the lone pair of electrons on the pyrrolidine N2 of (S)-cotinine to the π bond of the carbonyl group causes the pyrrolidine N2 to be hardly protonated, which significantly limits the cation-π interaction with the aromatic cage from the receptor and its action as an agonist.

Example 4

This example describes the effect of replacement of the pyrrolidine moiety of nicotine with a piperidine moiety.

The N-methyl pyrrolidine moiety of nicotine was replaced with a N-methyl piperidine moiety to study the effect of increasing the membrane ring on the stimulatory activity of Asu-ACR-16. N-methyl anabasine was inactive, but when the N-methyl group of the piperidine was removed, the compound was a potent agonist. The piperidine ring of (S)-anabasine may sterically and electrostatically stabilize the aromatic cage on the receptor better than the N-methylated pyrrolidine ring of nicotine.

The novel lead compound, (S)-5-ethynyl-anabasine, contains two moieties favorable to the Asu-ACR-16 ligand-binding site, namely an electron-withdrawing group at the 5-pyridine of the nicotine moiety ((S)-SIB 1508Y) and the piperidine moiety ((S)-anabasine). (S)-5-ethynyl-anabasine shows high potency ($EC_{50}$ 0.14±0.01 μM, N=5) as an agonist.

Example 5

This example describes the synthesis of (S)-5-bromonicotine.

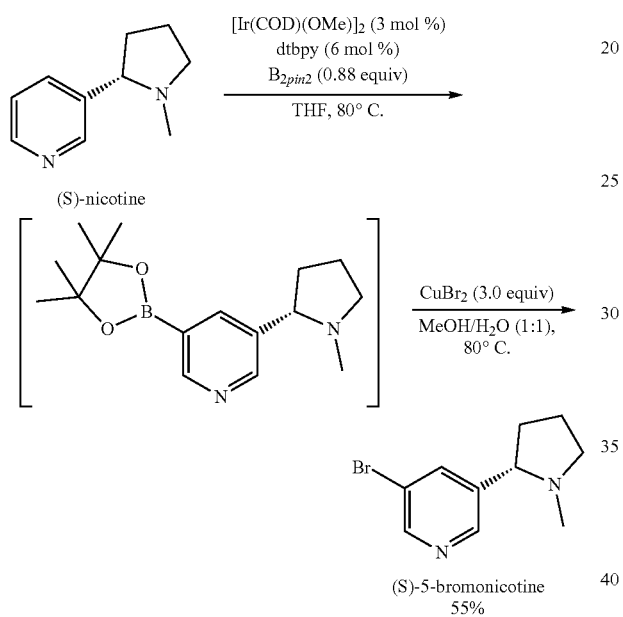

See Liskey et al., JACS 132(33): 11389-11391 (2010)). [Ir(COD)(OMe)]$_2$ is di-μ-methoxobis(1,5-cyclooctadiene)diiridium(I). dtbpy is 4,4'-di-tert-butyl-2,2'-dipyridyl. B$_2$pin$_2$ is bis(pinacolato)diboron. THF is tetrahydrofuran. CuBr$_2$ is copper(II) bromide. MeOH is methanol.

Example 6

This example describes the synthesis of (S)-tert-butyl-2-(pyridine-3-yl)piperidine-1-carboxylate.

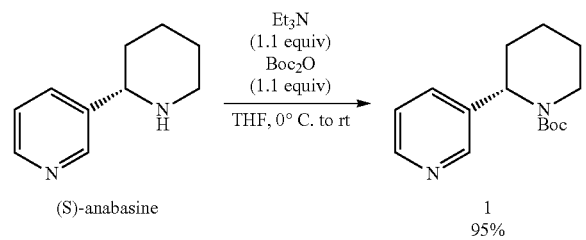 [SMILES: c1cncc([C@@H]2CCCCN2)c1 ; CC(C)(C)OC(=O)N1CCCC[C@H]1c1cccnc1]

Di-tert-butyl dicarbonate (Boc$_2$O; 3.30 g, 15.1 mmol, 1.10 equiv) was added to a solution of (S)-anabasine (2.23 g, 13.7 mmol, 1.0 equiv) and trethylamine (Et$_3$N; 2.10 mL, 15.1 mmol, 1.10 equiv) in THF at 0° C. The reaction mixture was stirred for 10 min and warmed to room temperature. After stirring for 2 hr, the mixture was diluted with water and extracted with ethyl acetate (EtOAc) three times. The organic layers were combined, dried over Na$_2$SO$_4$, and concentrated under reduced pressure. The crude product was purified by flash column chromatography on silica gel (1:1 hexane:EtOAc) to yield compound 1, (S)-tert-butyl 2-(pyrin-3-yl)piperidine-1-carboxylate in 95% yield (3.40 g, 13.1 mmol) as a pale yellow liquid (confirmed by $^1$H NMR; spectral data matched the literature (Beng and Gawley, Organic Letters 13: 394-397 (2011)).

Example 7

This example describes the synthesis of (S)-tert-butyl 2-(5-bromopyridin-3-yl)piperidine-1-carboxylate.

Synthesis of compound 2, (S)-tert-butyl 2-(5-bromopyridin-3-yl)piperidine-1-carboxylate, from compound 1 was carried out as set forth below.

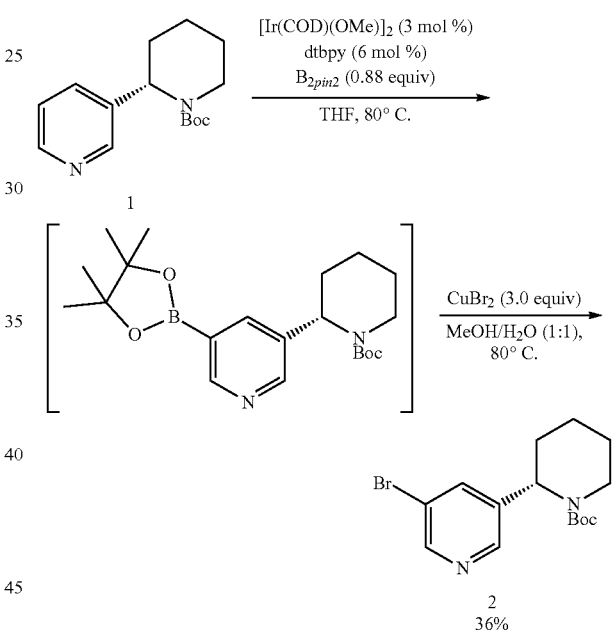

In a nitrogen-filled glove box compound 1 (1.31 g, 5.0 mmol), B$_2$pin$_2$ (1.12 mg, 4.4 mmol), [Ir(COD)(OMe)]$_2$ (99.5 mg, 0.150 mmol, 0.030 equiv), dtbpy (80.5 mg, 0.030 mmol, 0.060 equiv), and THF (8.0 mL) were combined in a vial. The reaction mixture was then sealed and heated at 80° C. for 16 hr. After the reaction mixture was cooled to room temperature, the volatiles were removed under vacuum. The residue was dissolved in 50.0 mL of MeOH and 50.0 mL of distilled water followed by CuBr$_2$ (3.35 g, 15.0 mmol). The flask was then sealed and heated at 80° C. for 16 hr. The reaction mixture was cooled to room temperature, and 30% NH$_4$OH (aq) (20.0 mL) was added to the reaction mixture. The reaction mixture was extracted with EtOAc three times, and the organic layers were combined, washed with brine, and dried over Na$_2$SO$_4$. The product was purified by column chromatography using silica gel (3:1 hexane:EtOAc) to give compound 2, (S)-tert-butyl 2-(5-bromopyridin-3-yl)piperidine-1-carboxylate, in 36% yield (618 mg, 1.80 mmol) as a pale yellow solid. $^1$H NMR (400 Hz, CDCl$_3$) δ 1.30-1.69 (m, 4H), 1.46 (s, 9H), 1.89-1.98 (s, 1H), 2.24 (dd, J=16.0, 2.0 Hz, 1H), 2.68-2.75 (m, 1H), 4.07 (d, J=15.6 Hz, 1H), 5.43 (s, 1H), 7.69 (s, 1H), 8.42 (s, 1H), 8.56 (s, 1H); $^{13}$C NMR (100.5 MHz, CDCl$_3$) δ 19.2, 25.0, 27.7, 28.3, 40.2, 51.2, 80.2, 120.9, 137.1, 138.1, 146.4, 148.8, 155.2; HRMS (ESI) calc'd. For $C_{15}H_{22}BrN_2O_2^+$ [M+H] 341.0859, found 341.0864. Note: for all Examples, chemical shifts are reported in ppm relative to a residual solvent peak (CDCl$_3$=7.26 ppm for $^1$H and 77.0 for $^{13}$C), and coupling constants are reported in hertz (Hz).

Example 8

This example describes the synthesis of (S)-5-bromoanabasine.

(S)-5-bromoanabasine was prepared from compound 2 as set forth below.

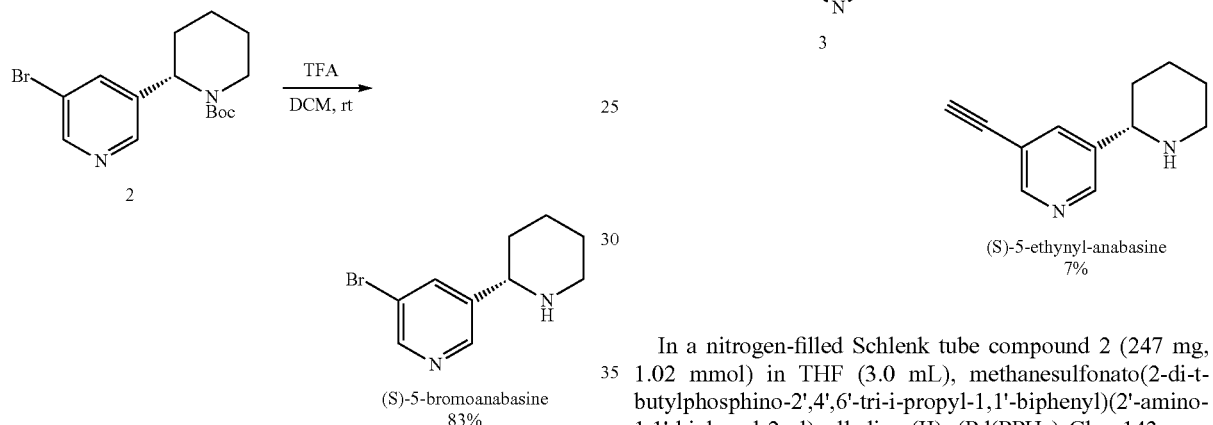

To a solution of compound 2 (93.0 mg, 0.273 mmol, 1.0 equiv) in dichloromethane (DCM; 5.0 mL), trifluoroacetic acid (TFA; 1.0 mL) was added dropwise. The reaction mixture was stirred at room temperature for 12 hr. The mixture was diluted with saturated NaHCO$_3$ and extracted with EtOAc three times. The organic layers were combined, dried over Na$_2$SO$_4$ and concentrated under reduced pressure. The crude product was purified by flash column chromatography on silica gel (10:1 hexane:EtOAc to 10:1 EtOAc:Et$_3$N) to give (S)-5-bromoanabasine in 83% yield (54.4 g, 0.226 mmol) as a pale yellow solid. $^1$H NMR (400 Hz, CDCl$_3$) δ 1.43-1.55 (m, 3H), 1.65-1.68 (m, 1H), 1.75-1.78 (m, 1H), 1.89 (brs, 2H), 2.74-2.80 (m, 1H), 3.18 (d, J=11.6 Hz, 1H), 3.61-3.63 (m, 1H), 7.89 (t, J=1.6 Hz, 1H), 4.7 (d, J=1.6 Hz, 1H), 8.53 (d, J=2.0 Hz, 1H); $^{13}$C NMR (151.0 MHz, CDCl$_3$) δ 25.0, 25.5, 34.8, 47.4, 59.1, 120.8, 136.9, 142.5, 146.7, 149.6; HRMS (ESI) calc'd. For $C_{10}H_{14}BrN_2^+$ [M+H] 241.0335, found 241.0332.

Example 9

This example describes the synthesis of (S)-5-ethynyl-anabasine.

(S)-5-ethynyl-anabasine was prepared from compound 2 as set forth below.

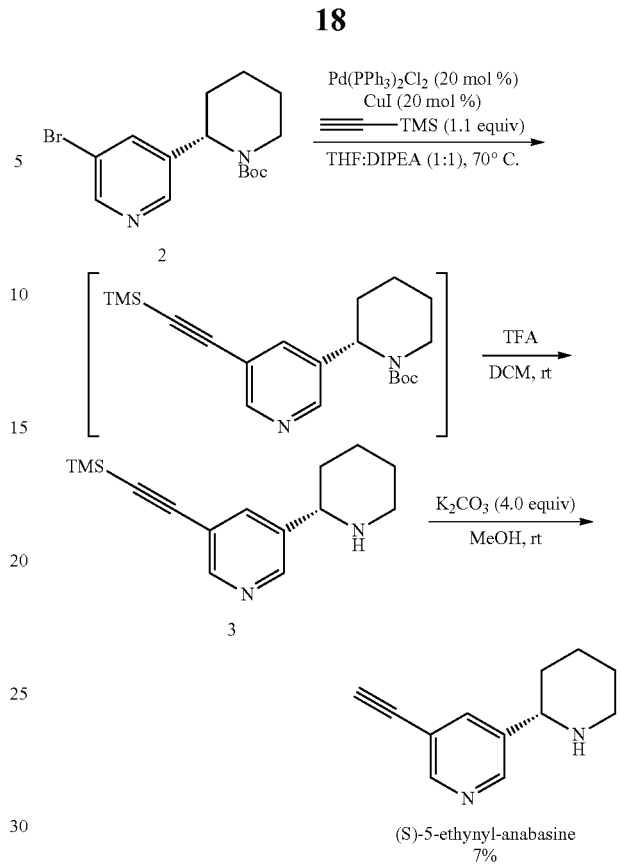

In a nitrogen-filled Schlenk tube compound 2 (247 mg, 1.02 mmol) in THF (3.0 mL), methanesulfonato(2-di-t-butylphosphino-2',4',6'-tri-i-propyl-1,1'-biphenyl)(2'-amino-1,1'-biphenyl-2-yl)palladium(II) (Pd(PPH$_3$)$_2$Cl$_2$; 143 mg, 0.204 mmol, 0.20 equiv), iodide (CuI; 39.0 mg, 0.204 mmol, 0.20 equiv), N,N-diisopropylethylamine (DIPEA; 3.0 mL), and trimethylsilylacetylene (0.16 mL, 1.12 mmol, 1.10 equiv) were added. The mixture was stirred at 70° C. for 16 hr. After cooling to room temperature, the mixture was filtered through a short pad of silica gel and washed with EtOAc. The filtrate was concentrated and purified by short silica gel column (100:1 hexane:EtOAc to hexane:EtOAc 5:1) to give the crude product, which was used directly for the next step.

To a solution of the crude product in DCM (10.0 mL) TFA (10.0 mL) was added. The mixture was stirred at room temperature for 2 hr. All of the volatiles were removed under reduced pressure. The crude product was purified by short silica gel column (2:1 hexane:EtOAc to 8:1 EtOAc:Et$_3$N).

To a solution of the above crude product in methanol (MeOH; 10.0 ml), K$_2$CO$_3$ (568 mg, 4.08 mmol) was added. The mixture was stirred at room temperature for 16 hr. After filtration and concentration, the product was purified by column chromatography using silica gel (5:1 hexane:EtOAc to 10:1 EtOAc:Et$_3$N) to give (S)-5-ethynyl-anabasine in 7% yield (12.8 mg, 0.0714 mmol) as a pale yellow liquid. $^1$H NMR (400 Hz, CDCl$_3$) δ 1.45-1.57 (m, 3H), 1.66-1.69 (m, 1H), 1.77-1.79 (m, 1H), 1.90 (brs, 1H), 2.07 (brs, 1H), 2.76-2.81 (m, 1H), 3.18 (s, 1H), 3.19 (d, J=12.0 Hz, 1H), 3.62-3.65 (m, 1H), 7.84 (t, J=2.0 Hz, 1H), 8.54 (s, 1H), 8.59 (s, 1H); HRMS (ESI) calc'd. For $C_{12}H_{15}N_2^+$ [M+H]$^+$ 187.1230, found 187.1232.

Example 10

This example describes the analysis of the potency of the agonists.

The nicotinic acetylcholine receptor subtype 16 from *Ascaris suum* (Asu-ACR-16) was selected as a pharmaceutical target. Nicotine was selected as a basic moiety ($EC_{50}$ 6.21±0.56 µM, $I_{max}$ 82.39±2.52%).

Full-length Asu-acr-16 cRNA and ancillary gene Asu-ric-3 cRNA (UniProtKB Accession No. F1L1D9) were prepared as previously described (Zheng et al. (2016), supra). A cRNA mixture of 25 ng Asu-acr-16 and 5 ng Asu-ric-3 cRNA in 50 nL RNAse-free water was injected into de-folliculated *Xenopus laevis* oocytes (Ecocyte Bioscience, Austin, Tex., USA). The injected oocytes were incubated in an incubation solution (100 mM NaCl, 2 mM KCl, 1.8 mM $CaCl_2.2H_2O$, 1 mM $MgCl_2.6H_2O$, 5 mM HEPES, 2.5 mM Na-pyruvate, 100 U/mL penicillin, and 100 µg/mL streptomycin, pH 7.5) at 19° C. for 4-8 days, after which 100 µM BAPTA-AM was added three hours before recording.

Two-electrode voltage clamp electrophysiology was used to determine agonist concentration-current-response plots to estimate the potencies ($EC_{50}$s) of the agonists. The oocytes were kept in a recording solution (100 mM NaCl, 2.5 mM KCl, 1 mM $CaCl_2.2H_2O$, and 5 mM HEPES, pH 7.3) and clamped to −60 mV during recording.

Inward current signals in the oocytes were induced by the addition of chemicals that acted as agonists opening the nicotinic ion-channel receptors. Specifically, acetylcholine chloride (ACh), (−)-nicotine hydrogen tartrate salt ((S)-nicotine), SIB 1508Y maleate ((S)-SIB 1508Y; Tocris Bioscience, Ellisville, Mo.), (S)-1-methylnicotinium iodide ((S)-1-methylnicotinium), (S)-1'-methylnicotinium iodide ((S)-1'-methylnicotinium), (+)-nornicotine (nornicotine), (−)-cotinine ((S)-cotinine), 6-aminonicotinamide (6-AN), (S)-anabasine, and (S,R)-anabasine (except for (S)-SIB 1508Y, all other chemicals were obtained from Sigma-Aldrich (St. Louis, Mo.) or Toronto Research Chemicals (Toronto, ON, Canada) were dissolved in recording solution. Polar compounds were initially dissolved in DMSO to make 100 mM stock solutions and then subsequently diluted in the recording solution to give a concentration of DMSO of <0.1%. An Axoclamp 2B amplifier (Molecular Devices, Sunnyvale, Calif.) was used to record the currents that were acquired with Clampex 9.2 software (Molecular Devices) and analyzed using GraphPad Prism 5.0 (Graphpad Software, Inc., La Jolla, Calif.).

Initially, 100 µM Ach was applied first to each oocyte for 10 sec to check for robust Asu-ACR-16 expression. In all oocyte recordings the peak current response to 100 µM ACh was used to normalize subsequent current responses in that oocyte. Recording solution was then used to wash out the drug from the oocyte for 3 min prior to application of the next chemical perfusion.

Nicotine derivatives that elicited inward currents at 100 µM were classified as agonists. Increasing concentrations of each nicotine derivative were applied for 10 sec with 3-min wash intervals to determine the dose-response relationship of each agonist. Downward responses to exposure of the agonists showed opening of the ion-channel. Peak responses were recorded and normalized. The dose-response relationships were described by the Hill equations to give estimates of the $EC_{50}$ (µM), Hill slope ($n_H$), and maximum response ($I_{max}$, %) and expressed as mean±S.E.M. (N=5) by using GraphPad Prism 5.0 (Graphpad). The $EC_{50}$ and $I_{max}$ of each agonist were compared using the unpaired student's t-test. P<0.05 was used to evaluate the statistical difference. In order to determine the rank order potency of the nicotine derivatives as antagonists, 100 µM ACh was applied for 10 sec, followed by a 10-sec co-application of 100 µM nicotine derivative with 100 µM ACh, and then a 10-sec wash of 100 µM ACh.

The $EC_{50}$ and $I_{max}$ for (S)-nicotine were 6.21±0.56 µM and 82.39±2.52%, N=5 (Table 2, which shows the pharmacological profiles of ACh, nicotine, and 15 nicotine derivatives; results (mean±S.E.M. were expressed as $EC_{50}$ (µM), Hill slope ($n_H$), and maximum response ($I_{max}$, %), and indicate the number of repeats of each agonist experiment ($N_{agonist}$), in which a single oocyte was used in each replicate). (S)-nicotine is a potent agonist of Asu-ACR-16, but can also activate mammalian nAChRs and, as an anthelmintic, would cause adverse side effects in the host (Chavez-Noriega et al., The Journal of Pharmacology and Experimental Therapeutics 280(1): 346-356 (1997)). As a low-molecular-weight and water-soluble molecule, (S)-nicotine was selected as an initial lead for further optimization (Bleicher et al., Nat Rev Drug Discov 2(5): 369-378 (2003)). Using (S)-nicotine as a pharmacophore and the predicted three-dimensional structures of Asu-ACR-16 ligand-binding site, the pharmacological properties of nicotine derivatives on Asu-ACR-16 were characterized. Of 15 nicotine derivatives tested, 12 derivatives acted as agonists. The agonist dose-response relationships for ACh and (S)-nicotine (FIG. 5A), pyridine-substituted nicotine derivatives (FIG. 5B), and the pyrrolidine-substituted nicotine derivatives (FIG. 5C) are shown. The pyridine N1-methylated substituent ((S)-1-methylnicotium), the 5'-carbonylated pyrrolidine substituent ((S)-cotinine), and the piperidine N2-methylated substituent (N-methyl anabasine) did not act as agonists.

TABLE 2

| Compound | $EC_{50}$ (µM) | $n_H$ | $I_{max}$ (%) | $N_{agonist}$ (# replicates) |
|---|---|---|---|---|
| (S)-5-ethynyl-anabasine | 0.14 ± 0.01 | 1.81 ± 0.24 | 79.33 ± 3.75 | 5 |
| (S)-5-bromo-anabasine | 0.32 ± 0.03 | 4.19 ± 1.58 | 80.69 ± 2.87 | 5 |
| (S)-SIB 1508Y | 0.37 ± 0.10 | 0.94 ± 0.04 | 100.1 ± 4.36 | 5 |
| 5-methyl-nicotine | 0.99 ± 0.17 | 2.09 ± 0.14 | 76.05 ± 1.22 | 5 |
| (S)-anabasine | 1.26 ± 0.19 | 2.26 ± 0.20 | 84.82 ± 4.20 | 5 |
| (S)-5-bromo-nicotine | 2.04 ± 0.12 | 2.46 ± 0.21 | 69.66 ± 3.28 | 5 |
| 6-methyl-nicotine | 6.13 ± 0.53 | 3.25 ± 0.25 | 69.75 ± 1.56 | 5 |
| (S)-nicotine | 6.21 ± 0.56 | 3.39 ± 0.36 | 82.39 ± 2.52 | 5 |
| ACh | 6.36 ± 0.49 | 2.93 ± 0.13 | 97.42 ± 0.93 | 5 |
| (S)-1'-methyl-nicotinium | 10.25 ± 0.62 | 3.52 ± 0.26 | 93.38 ± 5.25 | 5 |
| (S)-nicotine-5-carboxaldehyde | 11.51 ± 0.63 | 8.61 ± 4.04 | 62.20 ± 6.80 | 5 |

TABLE 2-continued

| Compound | $EC_{50}$ (μM) | $n_H$ | $I_{max}$ (%) | $N_{agonist}$ (# replicates) |
|---|---|---|---|---|
| 6-AN | 12.18 ± 0.29 | 10.10 ± 0.15 | 6.29 ± 0.62 | 5 |
| homonicotine | 16.62 ± 1.44 | 6.78 ± 2.50 | 22.01 ± 1.39 | 5 |
| nornicotine | 25.73 ± 4.71 | 3.25 ± 0.49 | 62.64 ± 3.42 | 5 |
| N-methyl-anabasine | <100 | | | |
| (S)-1-methyl-nicotinium | <100 | | | |
| (S)-cotinine | <100 | | | |

The rank order of potency based on the $EC_{50}$ values was: (S)-5-ethynyl-anabasine>(S)-5-bromoanabasine≈(S)-SIB 1508Y>5-methylnicotine≈(S)-anabasine>(S)-5-bromonicotine>6-methylnicotine≈(S)-nicotine≈ACh>(S)-1'-metylnicotinium≈(S)-nicotine-5-carboxyaldehyde≈6-AN>homonicotine≈nornicotine (Table 2). Two piperidine ring derivatives, namely (S)-5-bromoanabasine and (S)-anabasine, and two 5-substituted pyridine derivatives, namely (S)-SIB 1508Y and 5-methylnicotine, are more potent than ACh and (S)-nicotine (P<0.05, N=5). The $EC_{50}$ of the novel lead compound, (S)-5-ethynyl-anabasine, is 44 times lower (more potent) than its initial pharmacophore, (S)-nicotine, and is the most potent agonist of Asu-ACR-16 examined ($EC_{50}$ 0.14±0.01 μM).

The rank order of efficiency based on $I_{max}$ was: (S)-SIB 1508Y≈ACh≈(S)-1'-methylnicotinium≈(S)-anabasine≈(S)-nicotine≈(S)-5-bromoanabasine≈(S)-5-ethynyl-anabasine≈5-methylnicotine>6-methylnicotine≈(S)-5-bromonicotine z nornicotine≈(S)-nicotine-5-carboxyaldehyde>homonicotine>6-AN (Table 2). (S)-SIB 1508Y is more efficacious than (S)-nicotine (P<0.05, N=5), whereas (S)-1'-methylnicotinium and (S)-anabasine are not significantly more efficacious than (S)-nicotine (P>0.05, N=5).

The selected nicotine derivatives all inhibited the ACh response for Asu-ACR-16 at 100 μM. The rank order of inhibition was: 6-AN≈(s)-ethynyl-anabasine>homonicotine≈(S)-5-bromonicotine≈5-methylnicotine≈(S)-5-bromoanabasine≈6-methylnicotine≈(S)-nicotine-5-carboxyaldehyde≈(S)-SIB 1508Y≈N-methyl anabasine>(S)-1-methylnicotinium≈(S)-anabasine≈nornicotine>(S)-1'-methylnicotinium>(S)-cotinine (Table 2). 6-AN was the most potent inhibitor at 100 μM. Its $IC_{50}$ was 2.00±0.41 μM, its $n_H$ was 1.02±0.05, its $I_{max}$ was 94.88±1.49% (N=5) (FIG. 6). The inhibition (%) of 6-AN on ACh responses was not only concentration-dependent but also voltage dependent (FIG. 6), which strongly suggests that it acts as an open-channel blocker (Quek et al., ACS Chemical Neuroscience 1(12): 796-809 (2010)). The Ach dose-response curves in the presence of 1 μM 6-AN showed a reduction in $I_{max}$ with little shift of $EC_{50}$ (FIG. 6). Thus, 6-AN is a potent, non-competitive antagonist of Asu-ACR-16.

The selected nicotine derivatives in high doses showed 'rebound' tail current responses after the 10-sec drug application (FIGS. 8A-8K and FIGS. 9A-9D), which may be explained by the unblocking of the ion channel (Webster et al., British Journal of Pharmacology 127(6): 1337-1348 (1999)). The 'rebound' tail current response following wash-off of 10 μM (S)-5-bromoanabasine was pronounced (FIG. 12B). In addition, the voltage-sensitive inhibition (%) relationship was observed in a derivative with a protonated $N^+$. This property is consistent with the feature of open-channel blockers whereby the organic cation is drawn into, and then trapped in, the ion-channel pore under the influence of the strong voltage gradient (Rossokhin et al., Molecular and Cellular Neuroscience 63: 72-82 (2014)).

Both stimulatory effects and inhibitory effects were observed for several nicotine derivatives. 6-AN, the most potent Asu-ACR-16 inhibitor, behaved as a non-competitive antagonist. The results of electrophysiology showed 6-AN and other nicotine alkaloids are open-channel blockers of Asu-ACR-16, which can explain the non-competitive antagonism. Since all of these nicotine alkaloids have a protonated tertiary amine or tetramethyl ammonium moiety, the cationic nitrogen can interact with the aromatic cage in the agonist-binding site of the receptor and with the channel pore, thereby interfering with channel gating. The ligands initially bind to the agonist-binding site and turn the channel from the resting, closed state, to the open state, during which ions flow through the channel pore. When the channel is open, extra ligands bind to the inside of the channel pore, inhibit the current response, and prevent the dissociation of the ligand at the orthosteric site (Jackson, The Journal of Physiology 588(Pt 4): 553-554 (2010)).

Example 11

This example describes the analysis of the selectivity of (S)-5-ethynyl-anabasine and derivatives thereof for nematode parasite nAChRs over vertebrate homologs.

Molecular Docking

ACR-16 sequences are available in UniProtKB under their different accession numbers, e.g. Asu-Asc-16 is F1KYJ9 (see [SEQ ID NO: 1]; FIG. 1A). Three crystal structures of a human α7 nAChR chimera co-crystallized with ligands of different modes of action are used as templates to build different bound-form models of the extracellular domains (Huang et al. (2013), supra; Li et al., 2011; Zheng et al., 2016). Smiles strings of nicotine analogues and (S)-5-ethynyl-anabasine are obtained from the ZINC website (http:// at zinc.docking.org/search/structure) and converted to PDBQT format for docking studies. Docking of these ligands is performed at the orthosteric ligand-binding sites of agonist-bound, apo (no ligand) and antagonist-bound forms of the ECD-Asu-ACR-16 models using AutoDock Vina Software (Trott and Olson, 2010; Zheng et al. (2016), supra). The binding energies of the vertebrate nAChRs are compared with the binding energies of the nematode nAChRs and used to predict potency and selectivity. These in silico predictions of selectivities for nematode vs. vertebrate receptors are made on a basis of which agonist has a higher binding energy. If there is no selectivity, the binding energies are the same.

Agonist Potencies on Expressed Receptors

Full-length cRNA of Asu-acr-16 and human α7 nicotinic receptors and the ancillary gene, ric-3 (UniProtKB accession number: F1L1D9), are prepared using methods as previously described (Zheng et al. (2016), supra). A cRNA mixture of 25 ng Asu-acr-16 and 5 ng Asu-ric-3 cRNA in 50 nL RNAse-free water is injected into de-folliculated *Xenopus laevis* oocytes (Ecocyte Bioscience, Austin, Tex., USA) for ACR-16 receptors. A mixture of 25 ng of human α7 cRNA and 5 ng of human ric-3 cRNA in 50 nL RNAse-free water is injected into de-folliculated *Xenopus laevis* oocytes (Ecocyte Bioscience, Austin, Tex., USA) for α7 receptors. The injected oocytes are incubated in incubation solution at 19° C. for 4-8 days, with 100 μM BAPTA-AM added ~3 h before recording.

A two-electrode voltage-clamp technique is used to record separately currents from the Asu-ACR-16 receptors and the human α7 receptors expressed in the *Xenopus* oocytes. The oocytes are kept in recording solution and clamped to −60 mV. Inward current signals are induced by the addition of chemicals that act as agonists opening the nicotinic ion-channel receptors. An Axoclamp 2B amplifier (Molecular Devices, Sunnyvale, Calif.) is used to record the currents that are acquired with Clampex 9.2 (Molecular Devices, Sunnyvale, Calif.) software and analyzed using GraphPad Prism 5.0 (GraphPad Software Inc., La Jolla, Calif.). The $EC_{50}$s for the different compounds are recorded and used to determine the potency and selectivity of the agonists of the nematode ACR-16 vs. the vertebrate nicotinic receptors.

Example 12

This example describes the analysis of the toxicity of (S)-5-ethynyl-anabasine and derivatives thereof for nematode parasites.

Contraction Paralysis

Body flaps (1 cm) are prepared from the anterior regions of *A. suum*. Each flap is monitored isometrically on a force transducer in an experimental bath. After dissection, the preparations are allowed to equilibrate for 15 min under an initial tension of 2.0 g. The compounds are added cumulatively with 2-3 minute intervals between applications, and the responses are steady changes in tension. The responses for each concentration are measured as the gram force tension produced and also expressed as the % of the maximum contraction.

Changes in isometric muscle tension responses are monitored using a PowerLab System (AD Instruments, Colorado Springs, Colo.) consisting of the PowerLab hardware unit and Chart for Windows software. Sigmoid dose-response curves for each individual flap preparation at each concentration of antagonist are fitted using Prism 5.01 (GraphPad Software, Inc., La Jolla, Calif.) to estimate the constants by non-linear regression for each group of preparations receiving the same treatment. In preparations where desensitization is evident, the maximum response is used for fitting. The agonist concentration-response relationship at each concentration of antagonist is described by the lines best fitted to the Hill equation (variable slope, nH and maximum 100%). The potency of the contraction/spastic paralysis is measured.

Larval Migration $L_3$ isolates of parasite nematode larvae are maintained between passages in tap water refrigerated at 11° C. after collection from parasitic eggs and incubation to allow development of the $L_3$ larvae. $L_3$s (1,500-3,000) are ex-sheathed by 5-10 min incubation in 1.5% sodium hypochlorite solution. The larvae are then washed three times in migration buffer with the help of centrifugation (5 min, 1,000 g). Larvae (n=150) are collected with a pipette and placed in each of the compound concentrations to be tested for 2 h at 37° C. After incubation, $L_3$ larvae are re-suspended in fresh test solutions. The migration apparatus is made of two tightly fitting plastic tubes (~10 mm length) secured to a 20 m nylon filter placed in each test solution of a 24-well plate. The re-suspended larvae are added to the top of each filter, allowed to migrate through the filters and into the wells during incubation for 2 h at 37° C. At the end of the incubation period, the number of larvae remaining within each of the filter tubes is counted, and the number of larvae entering into the 24 well-plates is also counted. The percentage of larvae not migrating for each of the concentrations is then calculated. The relationship between the concentration of compound and the percentage of inhibited larvae is then examined by fitting the Hill equation to describe the sigmoidal dose-response curves. Toxic compounds have a potent inhibitory effect on migration.

Egg Hatching

Nematode eggs are isolated from fresh feces by centrifugation and flotation. The eggs are washed and inspected to confirm embryonation has not started. Each sample is tested at six concentrations of a test compound (e.g., 0.02, 0.05, 0.1, 0.25, 0.5 and 1.0 μg/ml) and a negative control (no compound). After incubation for 48 h, the assay is ended, and all eggs and larvae present in each well are counted. The Hill equation with a variable slope is used to fit the dose-response relations using GraphPad Prism. The $EC_{50}$-values and 95% confidence intervals are calculated. A potent compound inhibits egg hatching at low concentrations.

All patents, patent application publications, journal articles, textbooks, and other publications mentioned in the specification are indicative of the level of skill of those in the art to which the disclosure pertains. All such publications are incorporated herein by reference to the same extent as if each individual publication were specifically and individually indicated to be incorporated by reference.

The invention illustratively described herein may be suitably practiced in the absence of any element(s) or limitation(s), which is/are not specifically disclosed herein. Thus, for example, each instance herein of any of the terms "comprising," "consisting essentially of," and "consisting of" may be replaced with either of the other two terms. Likewise, the singular forms "a," "an," and "the" include plural references unless the context clearly dictates otherwise. Thus, for example, references to "the method" includes one or more methods and/or steps of the type, which are described herein and/or which will become apparent to those ordinarily skilled in the art upon reading the disclosure.

The terms and expressions, which have been employed, are used as terms of description and not of limitation. In this regard, where certain terms are defined under "Definitions" and are otherwise defined, described, or discussed elsewhere in the "Detailed Description," all such definitions, descriptions, and discussions are intended to be attributed to such terms. There also is no intention in the use of such terms and expressions of excluding any equivalents of the features shown and described or portions thereof. Furthermore, while subheadings, e.g., "Definitions," are used in the "Detailed Description," such use is solely for ease of reference and is not intended to limit any disclosure made in one section to that section only; rather, any disclosure made under one subheading is intended to constitute a disclosure under each and every other subheading.

It is recognized that various modifications are possible within the scope of the claimed invention. Thus, it should be understood that, although the present invention has been specifically disclosed in the context of preferred embodiments and optional features, those skilled in the art may resort to modifications and variations of the concepts disclosed herein. Such modifications and variations are considered to be within the scope of the invention as claimed herein.

What is claimed is:

1. The compound (S)-5-ethynyl-anabasine.

2. A composition comprising (i) the compound of claim 1 and (ii) a carrier.

3. The composition of claim 2, further comprising one or more other compounds having acetylcholine receptor-modulating activity.

4. The composition of claim 2, further comprising one or more other compounds having ascaricidal and/or nematicidal activity.

5. A method of making the compound of claim 1, which method comprises:
   (a) adding di-tert-butyl dicarbonate to a solution of (S)-anabasine and triethylamine in tetrahydrofuran (THF) at around 0° C. to form a first reaction mixture,
   (b) diluting the first reaction mixture with water and extracting the diluted first reaction mixture with ethyl acetate (EtOAc) to provide a first crude product,
   (c) purifying the first crude product to give (S)-tert-butyl 2-(pyrin-3-yl)piperidine-1-carboxylate,
   (d) adding methanesulfonato(2-di-t-butylphosphino-2',4',6'-tri-i-propyl- 1,1'-biphenyl)(2'-amino-1,1'-biphenyl-2-yl)palladium(II), iodide (CuI), N,N-diisopropylethylamine (DIPEA), and trimethylsilylacetylene to (S)-tert-butyl 2-(pyrin-3-yl)piperidine-1-carboxylate in THF to form a second reaction mixture,
   (e) filtering the second reaction mixture, washing the filtered second reaction mixture with EtOAc, and concentrating and purifying the filtrate to give a second crude product,
   (f) adding trifluoroacetic acid to a solution of the second crude product in dichloromethane,
   (g) removing all volatiles and purifying the second crude product,
   (h) adding $K_2CO_3$ to a solution of the second crude product in methanol, and
   (i) filtering, concentrating, and purifying the second crude product to give (S)-5-ethynyl-anabasine,
   whereupon (S)-5-ethynyl-anabasine is made.

6. A method of modifying the compound of claim 1, which method comprises independently substituting one or more ring hydrogens with a moiety selected from the group consisting of:
   alkyl, cycloalkyl, hydroxyalkyl, alkenyl, alkynyl, aryl, alkylaryl, arylalkyl, aryloxyalkyl, heterocyclic, trifluoromethyl, halo, cyano, cyanomethyl, nitro, —S(O)R', —S(O)$_2$R', —S(O)$_2$NHR', —NR$_2$', —C(O)R'', —OR', —OR''', —NR''', —SR', and —SR'''',
   wherein R' is hydrogen, alkyl, cycloalkyl, alkenyl, alkynyl, aryl, alkylaryl, arylalkyl, heterocyclic, trifluoromethyl, halo, cyano, or nitro,
   wherein R'' is hydrogen, alkyl, alkoxy, alkylamino, alkenyl, alkynyl, aryl, aryloxy, arylamino, alkylaryl, arylalkyl, heterocyclic, or trifluoromethyl, wherein R''' is hydrogen, alkyl, cycloalkyl, alkenyl, alkynyl, aryl, alkylaryl, arylalkyl, aroyl, heterocyclic, acyl, trifluoromethyl, alkylsulfonyl, or arylsulfonyl, wherein, when the moiety is NR''', R''' and the N to which it is attached can form a 4-, 5-, 6-, or 7-membered ring, wherein R'''' is hydrogen, alkyl, alkenyl, alkynyl, aryl, alkylaryl, arylalkyl, heterocyclic, or trifluoromethyl, wherein any of the aforementioned moieties can be substituted, and wherein the compound has acetylcholine receptor-modulating activity, whereupon (S)-5-ethynyl-anabasine is modified.

7. The composition of claim 3, wherein the one or more other compounds having acetylcholine receptor-modulating activity is a derivative of (S)-5-ethynyl-anabasine, which comprises a substitution of one or more ring hydrogens, wherein each substitution is a moiety independently selected from the group consisting of:

alkyl, cycloalkyl, hydroxyalkyl, alkenyl, alkynyl, aryl, alkylaryl, arylalkyl, aryloxyalkyl, heterocyclic, trifluoromethyl, halo, cyano, cyanomethyl, nitro, —S(O)R', —$S(O)_2$R', —$S(O)_2$NHR', —$NR_2$', —C(O)R'', —OR', —OR''', —NR''', —SR', and —SR'''', wherein R' is hydrogen, alkyl, cycloalkyl, alkenyl, alkynyl, aryl, alkylaryl, arylalkyl, heterocyclic, trifluoromethyl, halo, cyano, or nitro, wherein R'' is hydrogen, alkyl, alkoxy, alkylamino, alkenyl, alkynyl, aryl, aryloxy, arylamino, alkylaryl, arylalkyl, heterocyclic, or trifluoromethyl, wherein R''' is hydrogen, alkyl, cycloalkyl, alkenyl, alkynyl, aryl, alkylaryl, arylalkyl, aroyl, heterocyclic, acyl, trifluoromethyl, alkylsulfonyl, or arylsulfonyl, wherein, when the moiety is NR''', R''' and the N to which it is attached can form a 4-, 5-, 6-, or 7-membered ring, wherein R''''is hydrogen, alkyl, alkenyl, alkynyl, aryl, alkylaryl, arylalkyl, heterocyclic, or trifluoromethyl, wherein any of the aforementioned moieties can be substituted, and wherein the compound has acetylcholine receptor-modulating activity.

8. The composition of claim 7, further comprising one or more other compounds having ascaricidal and/or nematicidal activity.

* * * * *

SEQUENCE LISTING

<160> NUMBER OF SEQ ID NOS: 4

<210> SEQ ID NO 1
<211> LENGTH: 209
<212> TYPE: PRT
<213> ORGANISM: Ascaris suum

<400> SEQUENCE: 1

Tyr His Glu Arg Arg Leu Tyr Glu Asp Leu Met Arg Asp Tyr Asn Asn
1               5                   10                  15

Leu Glu Arg Pro Val Ala Asn His Ser Gln Pro Val Thr Val Tyr Leu
            20                  25                  30

Lys Val Ser Leu Gln Gln Ile Ile Asp Val Asp Glu Lys Asn Gln Ile
        35                  40                  45

Val Tyr Val Asn Ala Trp Leu Asp Tyr Ala Trp Asn Asp Tyr Lys Leu
50                  55                  60

Arg Trp Asp Lys Glu Glu Tyr Gly Asn Ile Thr Asp Val Arg Phe Pro
65                  70                  75                  80

Ala Gly Lys Ile Trp Lys Pro Asp Val Leu Leu Tyr Asn Ser Val Asp
            85                  90                  95

Ala Thr Leu Asp Ser Thr Tyr Pro Thr Asn Met Val Val Tyr Asn Thr
        100                 105                 110

Gly Asp Ile Ser Trp Ile Pro Pro Gly Ile Phe Lys Ile Ser Cys Lys
    115                 120                 125

Ile Asp Ile Lys Trp Phe Pro Phe Asp Glu Gln Arg Cys Phe Phe Lys
130                 135                 140

Phe Gly Ser Trp Thr Tyr Asp Gly Phe Lys Leu Asp Leu Gln Pro Gly
145                 150                 155                 160

Lys Gly Gly Phe Asp Ile Ser Glu Tyr Met Pro Ser Gly Glu Trp Ala
            165                 170                 175

Leu Pro Met Thr Thr Val Ser Arg Thr Glu Lys Phe Tyr Asp Cys Cys
        180                 185                 190

Pro Glu Pro Tyr Pro Asp Leu Thr Phe Tyr Leu His Met Arg Arg Arg
    195                 200                 205

Thr

<210> SEQ ID NO 2
<211> LENGTH: 206
<212> TYPE: PRT
<213> ORGANISM: Lymnaea stagnalis

<400> SEQUENCE: 2

Glu Phe Asp Arg Ala Asp Ile Leu Tyr Asn Ile Arg Gln Thr Ser Arg
1               5                   10                  15

Pro Asp Val Ile Pro Thr Gln Arg Asp Arg Pro Val Ala Val Ser Val
            20                  25                  30

Ser Leu Lys Phe Ile Asn Ile Leu Glu Val Asn Glu Ile Thr Asn Glu
        35                  40                  45

Val Asp Val Val Phe Trp Gln Gln Thr Thr Trp Ser Asp Arg Thr Leu
50                  55                  60

Ala Trp Asn Ser Ser His Ser Pro Asp Gln Val Ser Val Pro Ile Ser
65                  70                  75                  80

```
Ser Leu Trp Val Pro Asp Leu Ala Ala Tyr Asn Ala Ile Ser Lys Pro
                85                  90                  95

Glu Val Leu Thr Pro Gln Leu Ala Arg Val Val Ser Asp Gly Glu Val
            100                 105                 110

Leu Tyr Met Pro Ser Ile Arg Gln Arg Phe Ser Cys Asp Val Ser Gly
        115                 120                 125

Val Asp Thr Glu Ser Gly Ala Thr Cys Arg Ile Lys Ile Gly Ser Trp
    130                 135                 140

Thr His His Ser Arg Glu Ile Ser Val Asp Pro Thr Thr Glu Asn Ser
145                 150                 155                 160

Asp Asp Ser Glu Tyr Phe Ser Gln Tyr Ser Arg Phe Glu Ile Leu Asp
                165                 170                 175

Val Thr Gln Lys Lys Asn Ser Val Thr Tyr Ser Cys Cys Pro Glu Ala
            180                 185                 190

Tyr Glu Asp Val Glu Val Ser Leu Asn Phe Arg Lys Lys Gly
        195                 200                 205

<210> SEQ ID NO 3
<211> LENGTH: 204
<212> TYPE: PRT
<213> ORGANISM: Artificial
<220> FEATURE:
<223> OTHER INFORMATION: Synthetic

<400> SEQUENCE: 3

Glu Phe Gln Arg Lys Leu Tyr Lys Glu Leu Val Lys Asn Tyr Asn Pro
1               5                   10                  15

Asp Val Ile Pro Thr Gln Arg Asp Arg Pro Val Thr Val Tyr Phe Ser
            20                  25                  30

Leu Ser Leu Leu Gln Ile Met Asp Val Asp Glu Lys Asn Gln Val Val
        35                  40                  45

Asp Val Val Phe Trp Leu Gln Met Ser Trp Thr Asp His Tyr Leu Gln
    50                  55                  60

Trp Asn Val Ser Glu Tyr Pro Gly Val Lys Gln Val Ser Val Pro Ile
65                  70                  75                  80

Ser Ser Leu Trp Val Pro Asp Leu Ala Ala Tyr Asn Ala Ile Ser Lys
                85                  90                  95

Pro Glu Val Leu Thr Pro Gln Leu Ala Leu Val Asn Ser Ser Gly His
            100                 105                 110

Val Gln Tyr Leu Pro Ser Ile Arg Gln Arg Phe Ser Cys Asp Val Ser
        115                 120                 125

Gly Val Asp Thr Glu Ser Gly Ala Thr Cys Lys Leu Lys Phe Gly Ser
    130                 135                 140

Trp Thr His His Ser Arg Glu Leu Asp Leu Gln Met Gln Glu Ala Asp
145                 150                 155                 160

Ile Ser Gly Tyr Ile Pro Tyr Ser Arg Phe Glu Leu Val Gly Val Thr
                165                 170                 175

Gln Lys Arg Ser Glu Arg Phe Tyr Glu Cys Cys Lys Glu Pro Tyr Pro
            180                 185                 190

Asp Val Thr Phe Thr Val Thr Phe Arg Lys Lys Gly
        195                 200

<210> SEQ ID NO 4
<211> LENGTH: 207
<212> TYPE: PRT
<213> ORGANISM: Artificial
```

-continued

```
<220> FEATURE:
<223> OTHER INFORMATION: Synthetic

<400> SEQUENCE: 4

Glu Phe Gln Arg Lys Leu Tyr Lys Glu Leu Val Lys Asn Tyr Asn Pro
1               5                   10                  15

Leu Glu Arg Pro Val Ala Asn Asp Ser Gln Pro Leu Thr Val Tyr Phe
            20                  25                  30

Ser Leu Ser Leu Leu Gln Ile Met Asp Val Asp Glu Lys Asn Gln Val
        35                  40                  45

Leu Thr Thr Asn Ile Trp Leu Gln Met Ser Trp Thr Asp His Tyr Leu
    50                  55                  60

Gln Trp Asn Val Ser Glu Tyr Pro Gly Val Lys Thr Val Arg Phe Pro
65                  70                  75                  80

Asp Gly Gln Ile Trp Lys Pro Asp Ile Leu Leu Tyr Asn Ser Ala Asp
                85                  90                  95

Glu Arg Phe Asp Ala Thr Phe His Thr Asn Val Leu Val Asn Ser Ser
                100                 105                 110

Gly His Cys Gln Tyr Leu Pro Pro Gly Ile Phe Lys Ser Ser Cys Tyr
            115                 120                 125

Ile Asp Val Arg Trp Phe Pro Phe Asp Val Gln His Cys Lys Leu Lys
        130                 135                 140

Phe Gly Ser Trp Ser Tyr Gly Gly Trp Ser Leu Asp Leu Gln Met Gln
145                 150                 155                 160

Glu Ala Asp Ile Ser Gly Tyr Ile Pro Asn Gly Glu Trp Asp Leu Val
                165                 170                 175

Gly Ile Pro Gly Lys Arg Ser Glu Arg Phe Tyr Glu Cys Cys Lys Glu
            180                 185                 190

Pro Tyr Pro Asp Val Thr Phe Thr Val Thr Met Arg Arg Arg Thr
            195                 200                 205
```